( 12 ) United States Patent
Takakura et al.

(10) Patent No.: US 9,389,443 B2
(45) Date of Patent: Jul. 12, 2016

(54) DEVICE FOR INSPECTING A PHOTOELECTRIC PULSE WAVE SENSOR AND METHOD FOR INSPECTING A PHOTOELECTRIC PULSE WAVE SENSOR

(71) Applicant: KABUSHIKI KAISHA TOSHIBA, Tokyo (JP)

(72) Inventors: Junya Takakura, Kanagawa (JP); Kanako Nakayama, Tokyo (JP); Sawa Fuke, Kanagawa (JP); Takuji Suzuki, Kanagawa (JP); Yasunobu Yamauchi, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 27 days.

(21) Appl. No.: 14/490,098

(22) Filed: Sep. 18, 2014

(65) Prior Publication Data
US 2015/0116814 A1 Apr. 30, 2015

(30) Foreign Application Priority Data
Oct. 24, 2013 (JP) .................................. 2013-221064

(51) Int. Cl.
G02B 26/00 (2006.01)
G02F 1/29 (2006.01)
G02F 1/13 (2006.01)
(Continued)

(52) U.S. Cl.
CPC ................ G02F 1/1313 (2013.01); A61B 5/00 (2013.01); A61B 5/026 (2013.01); G02B 26/023 (2013.01); G02B 26/0816 (2013.01); G02F 1/13 (2013.01); A61B 5/0261 (2013.01)

(58) Field of Classification Search
CPC .. G02B 26/02; G02B 26/023; G02B 26/0816; G02F 1/13; G02F 1/1313; G02F 1/29; A61B 5/00; A61B 5/02116; A61B 5/024; A61B 5/0261; A61B 5/029; A61B 5/14532; A61B 5/1495
USPC ................. 359/238, 245, 290, 315, 318, 320; 600/316, 322, 430, 479, 490, 503; 601/150, 151
See application file for complete search history.

(56) References Cited

U.S. PATENT DOCUMENTS 3,602,213 A * 8/1971 Howell ................ A61B 5/0261
250/227.11
5,278,627 A 1/1994 Aoyagi et al.
(Continued)

FOREIGN PATENT DOCUMENTS

JP 4-261646 9/1992
JP 5-000135 1/1993
(Continued)

Primary Examiner — Loha Ben
(74) Attorney, Agent, or Firm — Nixon & Vanderhye, P.C.

(57) ABSTRACT

A device according to an embodiment includes: a simulated skin portion being located near a photoelectric pulse wave sensor to simulate a blood flow of the skin; a reflectance changing unit located on an opposite side of the simulated skin portion to the photoelectric pulse wave sensor, the reflectance changing unit changing, in time series, reflectance of light emitted from the light-emitting unit of the photoelectric pulse wave sensor and passing through the simulated skin portion; a reflectance change control unit that transmits a reflectance control signal to the reflectance changing unit to control changes in reflectance of the reflectance changing unit; and a synchronization signal output unit that outputs a signal in sync with the reflectance control signal to an external device.

11 Claims, 22 Drawing Sheets

(51) Int. Cl.
*G02B 26/02* (2006.01)
*G02B 26/08* (2006.01)
*A61B 5/026* (2006.01)
*A61B 5/00* (2006.01)

(56) References Cited

U.S. PATENT DOCUMENTS

| | | | | | |
|---|---|---|---|---|---|
| 5,514,079 | A | * | 5/1996 | Dillon | A61H 9/0078 128/DIG. 20 |
| 6,353,226 | B1 | * | 3/2002 | Khalil | A61B 5/14532 250/339.11 |
| 7,133,710 | B2 | * | 11/2006 | Acosta | A61B 5/0075 600/316 |
| 8,311,616 | B2 | * | 11/2012 | Feldman | A61B 5/04005 600/430 |
| 8,326,389 | B2 | * | 12/2012 | Epstein | A61B 5/14532 600/310 |
| 8,608,663 | B2 | | 12/2013 | Suzuki | |

FOREIGN PATENT DOCUMENTS

| | | |
|---|---|---|
| JP | 2007-319232 | 12/2007 |
| JP | 2009-189416 | 8/2009 |

\* cited by examiner

DEVICE FOR INSPECTING A PHOTOELECTRIC PULSE WAVE SENSOR AND METHOD FOR INSPECTING A PHOTOELECTRIC PULSE WAVE SENSOR

CROSS REFERENCE TO RELATED APPLICATIONS

This application is based upon and claims the benefit of priority from the prior Japanese Patent Application No. 2013-221064, filed on Oct. 24, 2013, the entire contents of which are incorporated herein by reference.

FIELD

Embodiments described herein relate generally to devices for inspecting photoelectric pulse wave sensor and methods for inspecting photoelectric pulse wave sensor.

BACKGROUND

It is known that if skin is irradiated with light from a light source including, for example, light-emitting diodes (LEDs), and if the reflected light is detected by a photosensor, the amount of reflected light has a pulsatile characteristic in response to the blood flow. Since the pulses of the reflected light correspond to heart beats, the number of heart beats can be estimated from the pulses. The number of heart beats can also be detected by irradiating skin with light, and detecting transmitted light on the other side of the skin. For example, a side of a finger opposite to the nail side is irradiated with light, and the light is detected on the nail side to detect the number of heart beats. These principles are employed in many biosensors intended for use in health care.

So far, the only way to inspect the performance of such biosensors has been to actually attach a biosensor to the skin of a human being and to measure the signals detected. However, it is impossible to keep constant the state of the blood flow of a human being and the state of the attachment of a biosensor. Therefore, it has been difficult to inspect biosensors under stable conditions.

A method of inspecting a biosensor detecting transmitted light has been proposed, in which pulsatile signals are simulated by mechanically inserting and removing a material having a light-absorbing property similar to that of blood into and from the space between a light source and a light-receiving sensor. However, if pulses having a frequency of 1 Hz are to be simulated in this method, the material simulating blood should be moved at a frequency of 1 Hz. Since applying this method causes mechanical vibrations in the inspection device itself, the light incident on the light-receiving unit of the biosensor also has a noise component of 1 Hz. This may lead to an erroneous inspection result indicating that pulses at a frequency of 1 Hz are detected although the biosensor does not meet the required performance.

DETAILED DESCRIPTION

A biosensor inspection device according to an embodiment is a device for inspecting a photoelectric pulse wave sensor of reflection type including: a simulated skin portion semitransparent to light, the simulated skin portion being located near the photoelectric pulse wave sensor to simulate a blood flow of the skin; a reflectance changing unit located on an opposite side of the simulated skin portion to the photoelectric pulse wave sensor, the reflectance changing unit changing, in time series, reflectance of light emitted from the light-emitting unit of the photoelectric pulse wave sensor and passing through the simulated skin portion; a reflectance change control unit that transmits a reflectance control signal to the reflectance changing unit to control changes in reflectance of the reflectance changing unit; and a synchronization signal output unit that outputs a signal in sync with the reflectance control signal to an external device.

Embodiments will now be explained in detail with reference to the accompanying drawings.

(First Embodiment)

Figure 1:
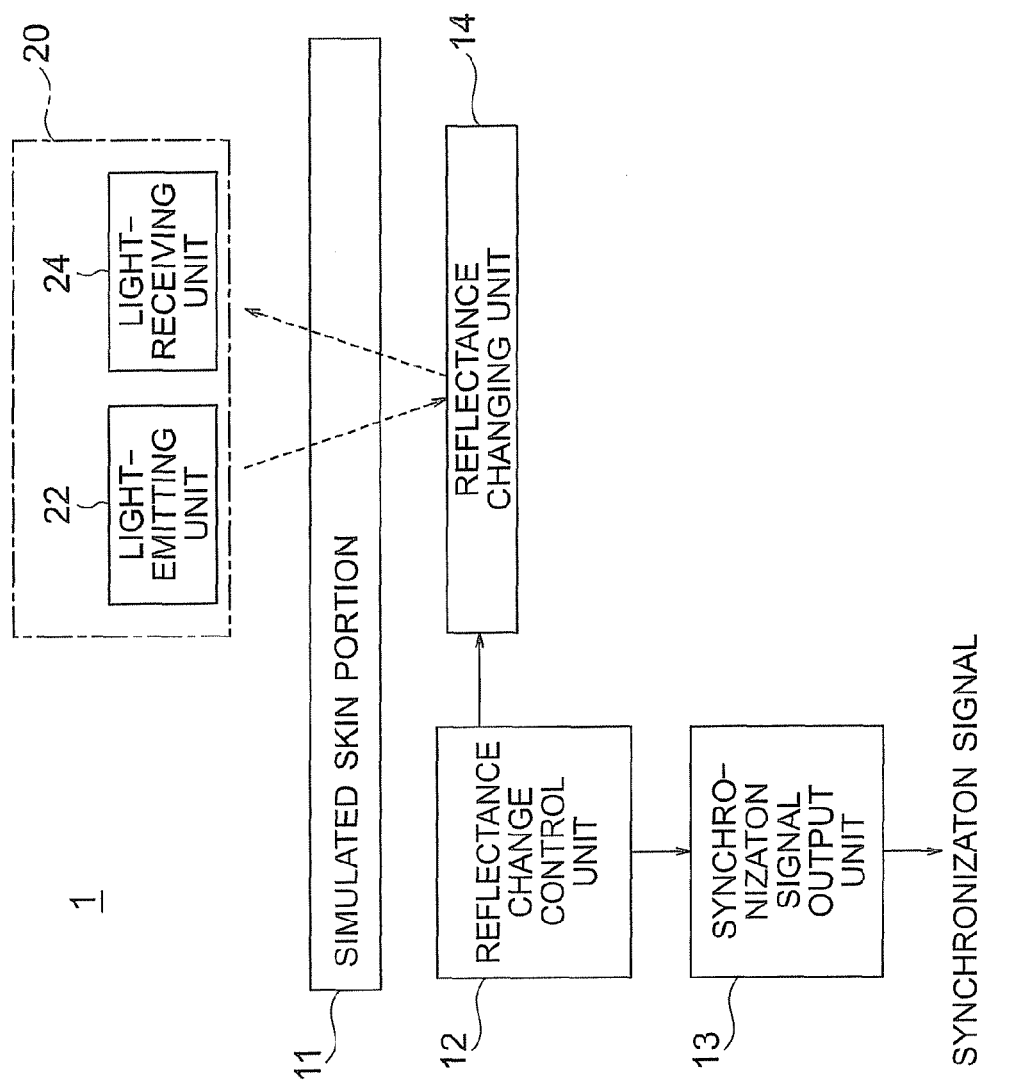
FIG. 1 is a block diagram showing a biosensor inspection device according to a first embodiment.
Figure 2:
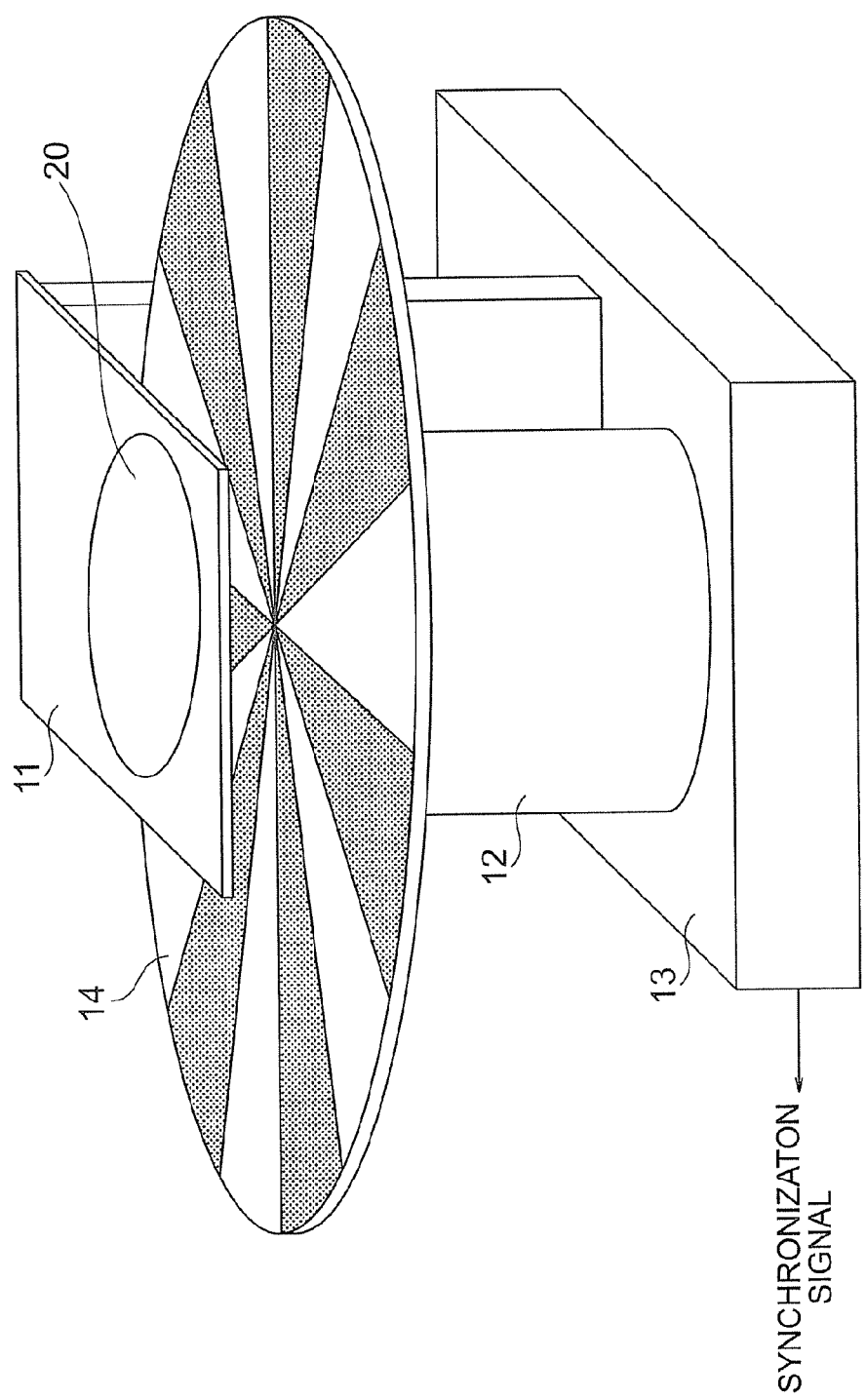
FIG. 2 is a perspective view briefly showing an appearance of the biosensor inspection device according to the first embodiment.
Figure 3:
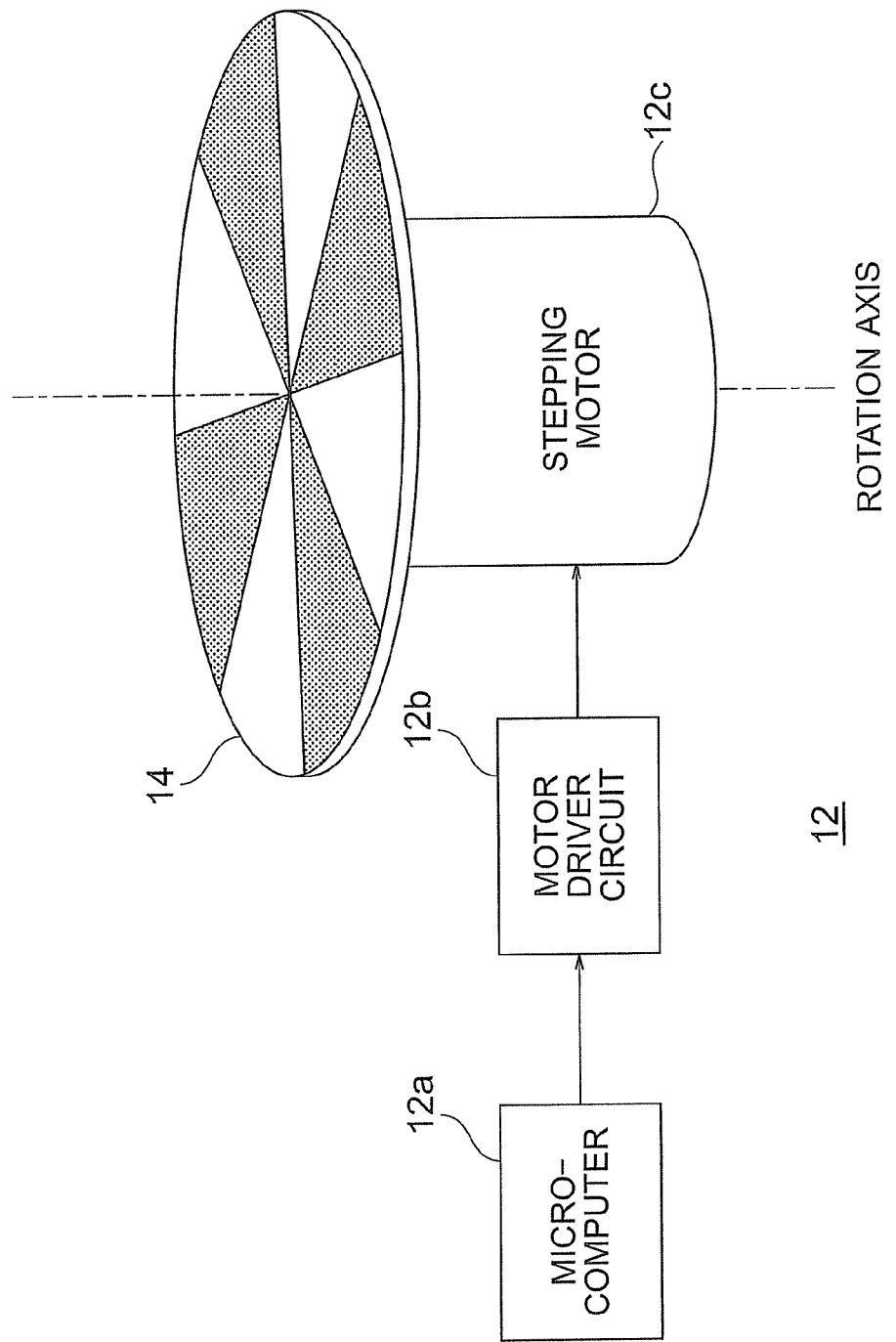
FIG. 3 is a diagram showing a relationship between a reflectance change control unit and a reflectance changing unit of the first embodiment.

A biosensor inspection device (hereinafter also referred to as an inspection device) according to a first embodiment will be described below with reference to FIGS. 1 to 3. FIG. 1 is a block diagram showing a biosensor inspection device 1 according to the first embodiment. FIG. 2 is a perspective view briefly showing an appearance of the biosensor inspection device 1.

The inspection device 1 according to the first embodiment inspects a photoelectric pulse wave sensor of reflection type 20 including a light-emitting unit 22 and a light-receiving unit 24. The photoelectric pulse wave sensor 20 is also referred to as a biosensor 20. The inspection device 1 includes a simulated skin portion 11, a reflectance change control unit 12, a synchronization signal output unit 13, and a reflectance changing unit 14.

The simulated skin portion 11 is for simulating light reflection and light scattering on the surface of skin of a living body, and located, for example, between the biosensor 20 and the reflectance changing unit 14 as shown in FIG. 2. The simulated skin portion 11 is made of a material semitransparent to light, and preferably has a Lambertian characteristic. The simulated skin portion 11 may be replaced depending on a person for whom the biosensor 20 is used.

The reflectance change control unit 12 transmits a reflectance control signal to the reflectance changing unit 14 to change the reflectance of the reflectance changing unit 14 in time series. The reflectance change control unit 12 may include, for example, a microcomputer 12a, a motor driver circuit 12b, and a stepping motor 12c as shown in FIG. 3. The microcomputer 12a transmits a drive signal to the motor driver circuit 12b to control the revolutions of the stepping motor 12c freely. The microcomputer 12a includes a memory to store predetermined control patterns of the stepping motor 12c. The reflectance change control unit 12 also has a function of transmitting, to the synchronization signal output unit 13, a signal in sync with the reflectance control signal for controlling the stepping motor.

The synchronization signal output unit 13 outputs, to an external device, a signal in sync with the change in reflectance indicating the state of the reflectance changing unit 14 in response to a signal in sync with the reflectance control signal outputted from the reflectance change control unit 12. The synchronization signal outputted from the synchronization signal output unit 13 serves as a reference signal when the photoelectric pulse wave sensor of reflection type 20 is inspected. The synchronization signal may be a simple digital signal on a transistor-transistor-logic (TTL) level, or a signal following a generally known protocol such as universal asynchronous receiver-transmitter (UART), inter-integrated circuit (I2C), and SPI (Serial Peripheral Interface).

Figure 4:
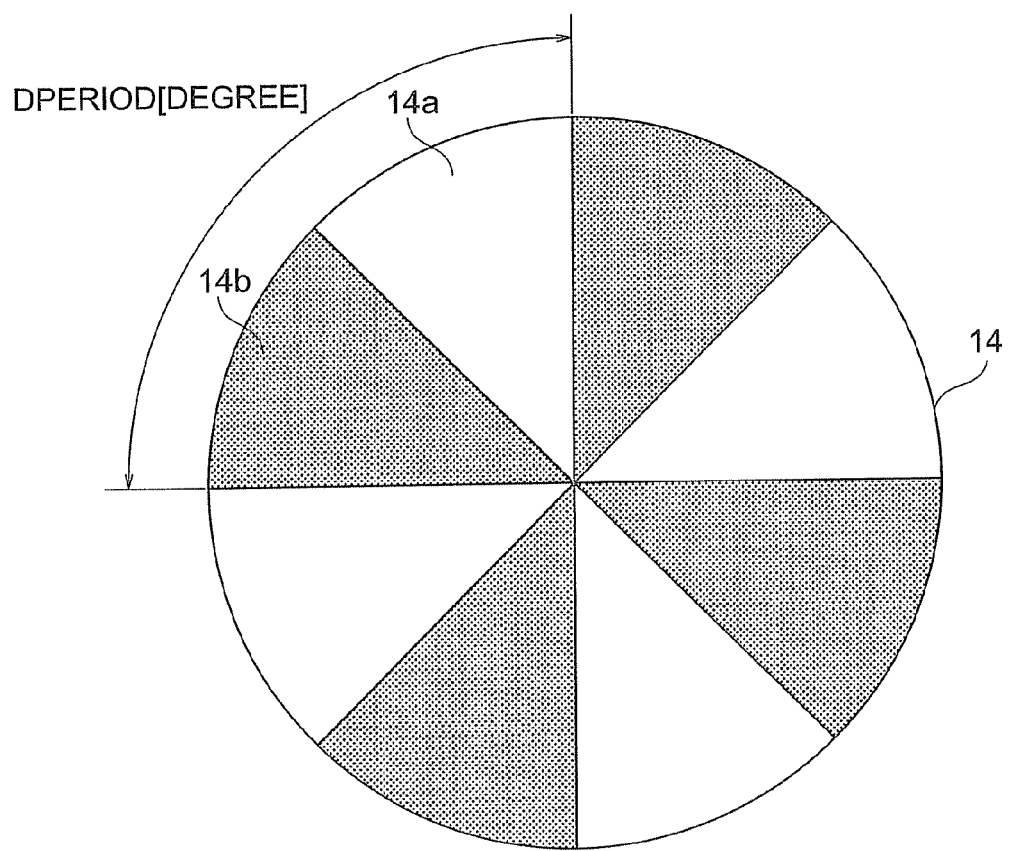
FIG. 4 is a diagram showing the reflectance changing unit of the first embodiment.

The reflectance changing unit 14 changes its reflectance in time series to simulate changes in the amount of light incident on the light-receiving unit 24 of the biosensor 20. In the first embodiment, the reflectance changing unit 14 is a disk on which portions 14a, 14b each having a different reflectance are printed so as to be arranged in the circumferential direction. Instead of printing the portions 14a, 14b, some elements formed of different materials with different reflectances may be bonded to the disk as the portions 14a, 14b. In the disk 14 shown in FIG. 4, sectors 14a with a greater reflectance and sectors 14b with a smaller reflectance are alternately arranged, adjacent sectors 14a and 14b forming a cycle Dperiod to so that the reflectance changes periodically. The disk 14 with the arrangement shown in FIG. 4 is driven by the stepping motor 12c of the reflectance change control unit 12 so as to rotate freely. The stepping motor 12c is controlled by the microcomputer 12a via the motor driver circuit 12b. The reflectance changing unit 14 of the first embodiment shown in FIG. 4 is a disk rotating in a plane parallel to a face opposed to the biosensor 20, as shown in FIG. 2. Therefore, the rotation axis of the reflectance changing unit 14 is perpendicular to the face opposed to the biosensor 20.

Figure 5:
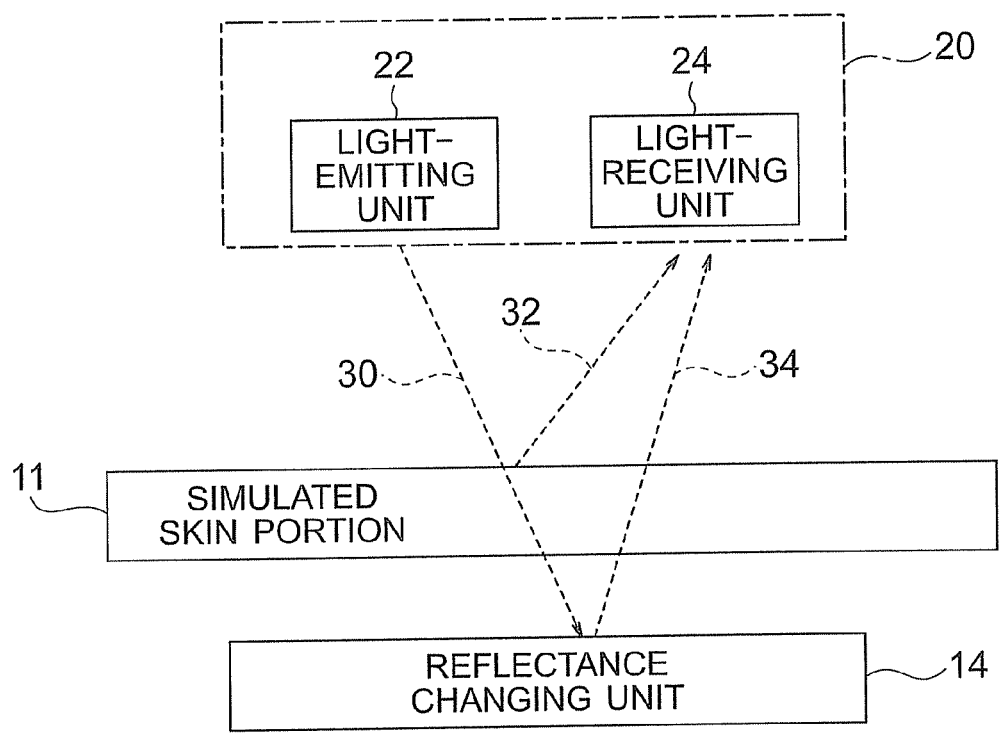
FIG. 5 is a diagram for explaining light paths in a photoelectric pulse wave sensor of reflection type used in the first embodiment.
Figure 6:
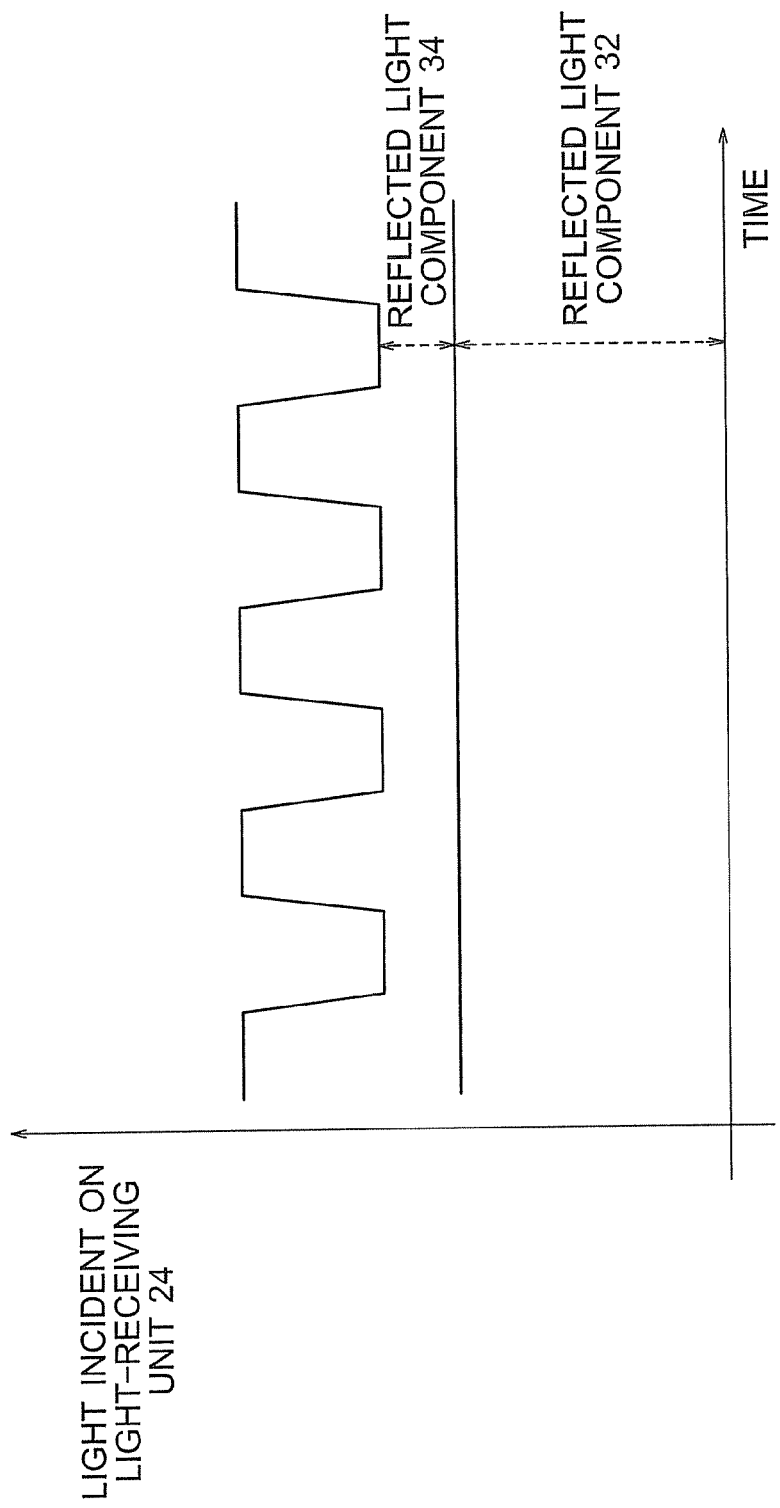
FIG. 6 is a diagram for explaining components of light detected by the photoelectric pulse wave sensor of reflection type.

The light-emitting unit 22 and the light-receiving unit 24 of the biosensor 20 are located on substantially the same plane. Therefore, the biosensor 20 may be located on the simulated skin portion 11 of the biosensor inspection device 1 according to the first embodiment as shown in FIG. 2. Partial light 32 of light 30 emitted from the light-emitting unit 22 is reflected on the surface of the simulated skin portion 11, and received by the light-receiving unit 24 without reaching the reflectance changing unit 14 as shown in FIG. 5. Partial light 34 passes through the simulated skin portion 11, is reflected on the surface of the reflectance changing unit 14, passes through the simulated skin portion 11 again, and reaches the light-receiving unit 24.

If the reflectance changing unit 14 rotates, the light reaching the light-receiving unit 24 of the biosensor 20 is a sum of a constant component corresponding to the light reflected by the simulated skin portion 11, i.e. reflected light component 32 and a varying component corresponding to the light reaching the reflectance changing unit 14, i.e. reflected light component 34. The waveform of the light becomes similar to that of a signal obtained from a photoelectric pulse wave sensor of reflection type 20 attached to an actual living body.

(Operation)

Next, the operation of the biosensor inspection device 1 according to the first embodiment will be described in detail with reference to a flow chart shown in FIG. 7.

First, the reflectance change control unit 12 sets the position of the disk serving as the reflectance changing unit 14 at a zero point (step 101). The zero-point setting may be performed by a certain mechanism such as a limit switch.

Next, the reflectance change control unit 12 transmits a command to the synchronization signal output unit 13 to output a synchronization signal. Receiving the command, the synchronization signal output unit 13 outputs a synchronization signal to the outside (step 102).

The reflectance change control unit 12 then transmits a drive signal to the reflectance changing unit 14 to drive the reflectance changing unit 14. The reflectance change control unit 12 includes a first counter (not shown) for counting the number of times the drive signal is transmitted, and increments a first count value, Nd, of the first counter by 1 every time the drive signal is transmitted (step 103).

The reflectance change control unit 12 determines whether the first count value Nd reaches a first predetermined value Nd_Limit (step 104). Assuming that the disk serving as the reflectance changing unit 14 rotates by Dd degrees in response to a drive signal, and the magnitude of reflectance periodically changes in a cycle of Dperiod (degree) as shown in FIG. 4, the first predetermined value Nd_Limit is determined by Nd_Limit=Dperiod/Dd. If the first count value Nd reaches the first predetermined value Nd_Limit, the first count value Nd is reset, i.e. Nd=0 and the process proceeds to step 105. The reflectance change control unit 12 also includes a second counter (not shown) to store the number of times the cycle of the variation in reflectance (second count value) Nbeat changes, and increments the second count value Nbeat by 1 every time the first count value Nd of the first counter reaches the first predetermined value Nd_Limit. If the first count value Nd is not equal to the first predetermined value Nd_Limit, the process returns to step 103, and the aforementioned steps are repeated.

The reflectance change control unit 12 determines whether the second count value Nbeat reaches a second predetermined value Nbeat_Limit (step 105). The second predetermined value Nbeat_Limit is a predetermined constant. If the second count value Nbeat reaches the second predetermined value Nbeat_Limit, the process ends. If the second count value Nbeat is not equal to the second predetermined value Nbeat_Limit, the process returns to step 102, and the aforementioned steps are repeated.

Figure 8:
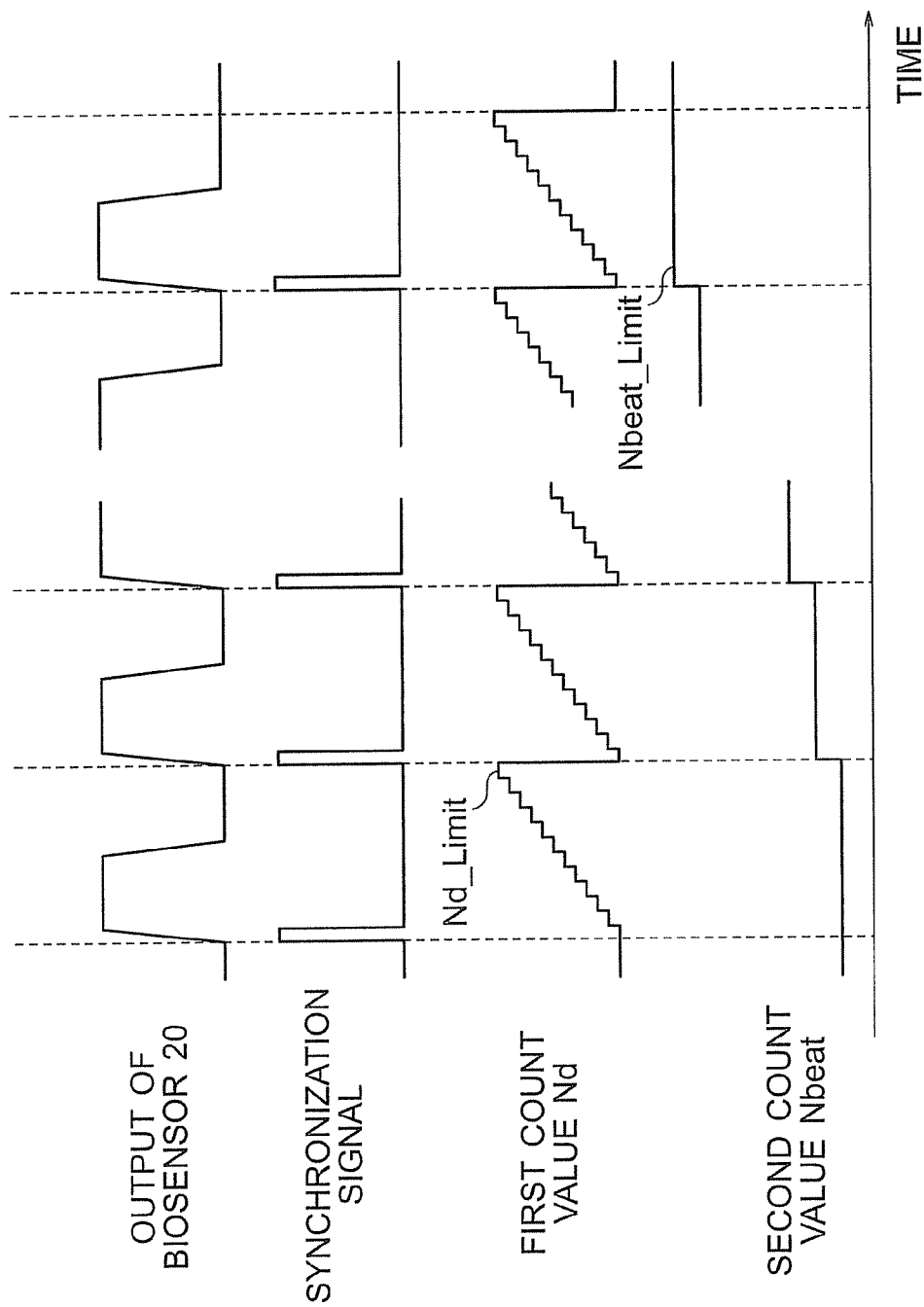
FIG. 8 shows waveforms of signals obtained by the biosensor inspection device according to the first embodiment.

As a result, signal waveforms shown in FIG. 8 are obtained. An inspection as to whether the biosensor 20 has a desired performance can be performed by checking the output of the biosensor 20.

Since the reflectance changes in a cycle that is different from the cycle of vibrations caused to the biosensor inspection device 1 itself of the first embodiment, an accurate inspection not affected by noise can be performed.

(First Modification)

Figure 9:
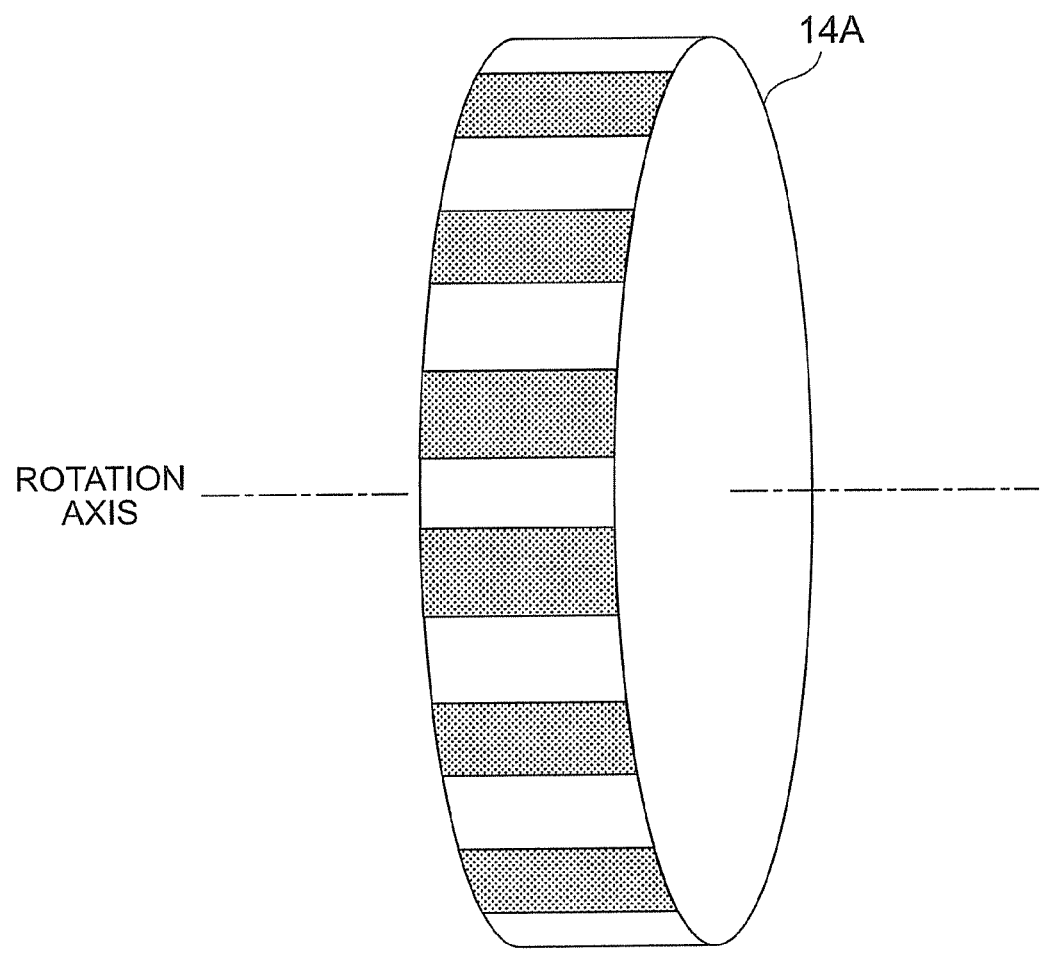
FIG. 9 is a perspective view of a reflectance changing unit of a first modification of the first embodiment.

A biosensor inspection device according to a first modification of the first embodiment will be described with reference to FIG. 9. The biosensor inspection device according to the first modification is obtained by replacing the reflectance changing unit 14 of the biosensor inspection device according to the first embodiment with a reflectance changing unit 14A shown in FIG. 9. The reflectance changing unit 14A includes portions 14Aa, 14Ab each having a different reflectance, which are printed on a side surface of a cylinder, as shown in FIG. 9. Unlike the case shown in FIG. 2, the reflectance changing unit 14A of the first modification shown in FIG. 9 is a cylinder rotating in a plane that is perpendicular to a face opposed to the biosensor 20. Therefore, the rotation axis of the reflectance changing unit 14A is in parallel with the face opposed to the biosensor 20.

Like the first embodiment, the reflectance of the first modification changes in a cycle that is different from the cycle of vibrations of the biosensor inspection device. Accordingly, an accurate inspection not affected by noise can be performed.

(Second Modification)

A biosensor inspection device according to a second modification of the first embodiment will be described with reference to FIGS. 10 and 11. The biosensor inspection device according to the second modification is obtained by replacing the reflectance changing unit 14 of the biosensor inspection device according to the first embodiment with a reflectance changing unit 14B shown in FIG. 10. The reflectance changing unit 14B includes portions 14Ba, 14Bb each having a different reflectance, which are printed on a flat plate. A plurality of pairs of portions 14Ba and 14Bb are printed on the flat plate. The reflectance changing unit 14B may have a mechanism including a pinion 14c and a rack 14d for converting rotational motion of the stepping motor to parallel motion, as shown in FIG. 11. The pinion 14c is located on the circumference of the rotation axis of the motor 12c, and the rack 14d is located on a surface of the flat plate opposite to the surface on which the portions 14Ba, 14Bb are printed.

Furthermore, a linear motor may be used instead of the stepping motor, the pinion 14c, and the rack 14d to move the reflectance changing unit 14B.

As in the case of the first embodiment, the reflectance in the second modification changes in a cycle that is different from the cycle of vibrations of the biosensor inspection device. Accordingly, an accurate inspection not affected by noise can be performed.

(Third Modification)

Average heart rate of a human being is approximately 60 beats per minute. The value changes depending on the circumstances, and may be 30 beats per minute or 200 beats per minute, for example. In order to perform an inspection of a biosensor using the biosensor inspection device according to the first embodiment in consideration of changes in heart rate, the number of revolutions of the motor is changed by increasing or decreasing the number of pulses of the drive signals transmitted to the motor in step 103 shown in FIG. 7.

Figure 12:
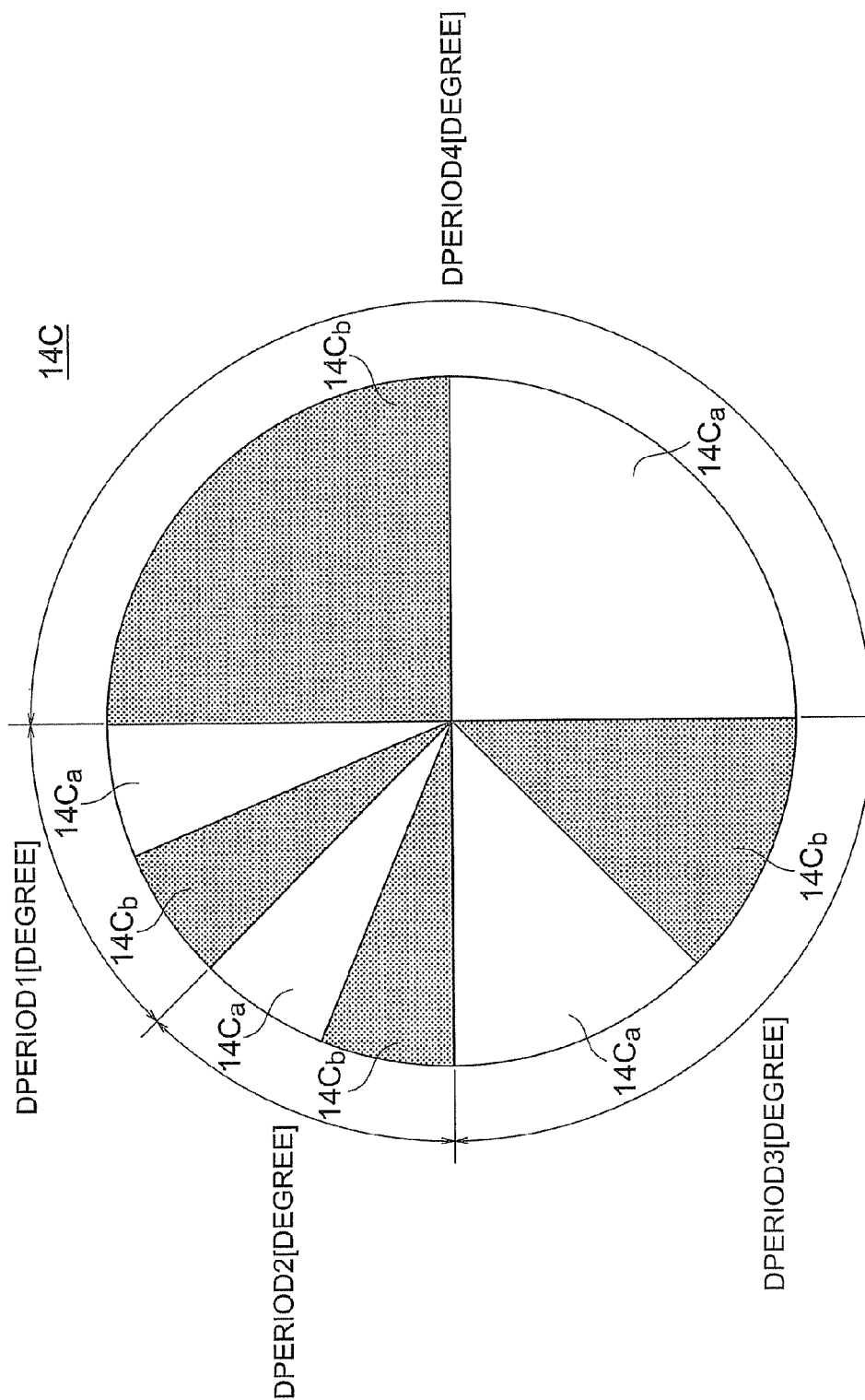
FIG. 12 is a plan view showing a reflectance changing unit of a third modification of the first embodiment.
Figure 13:
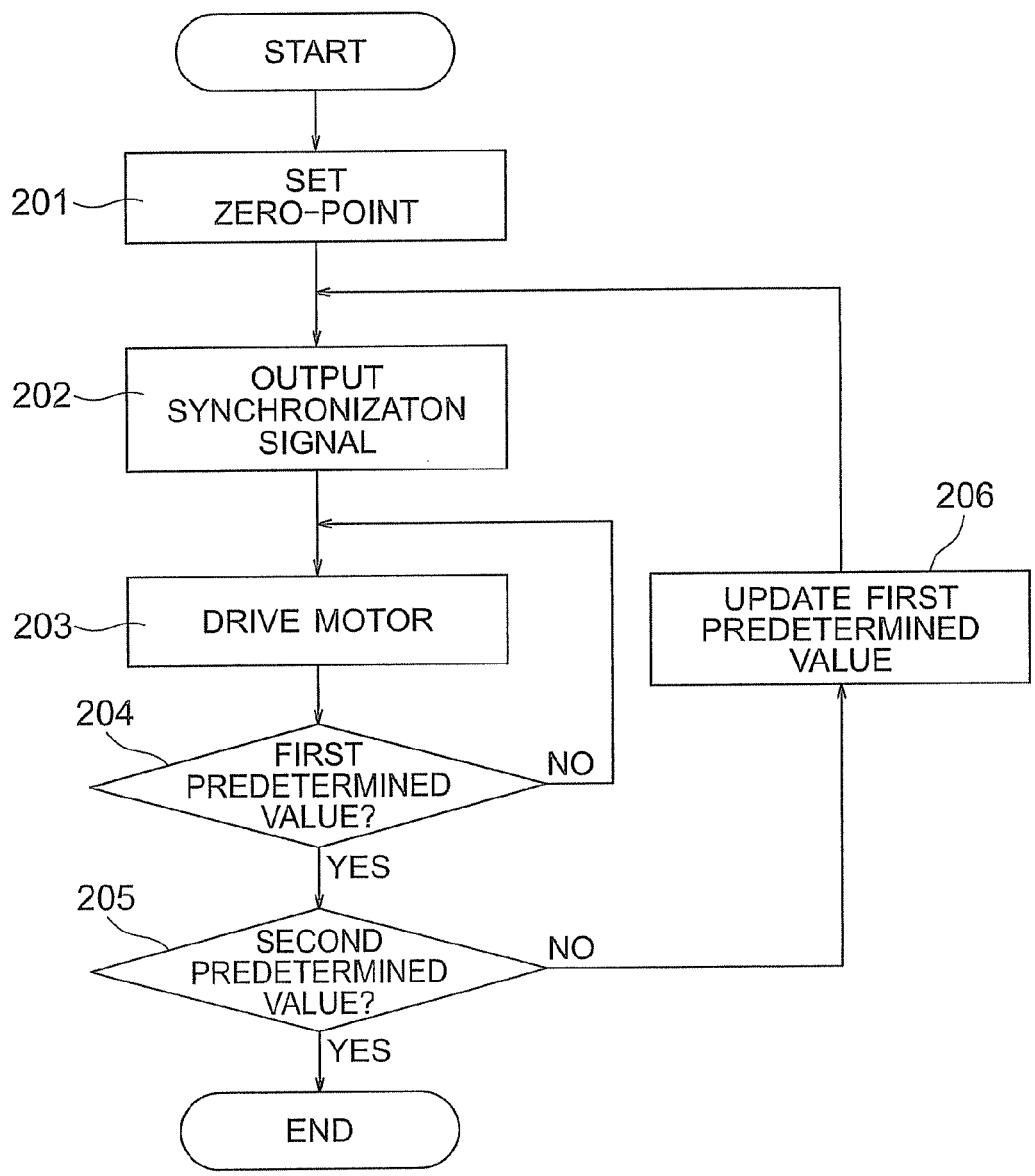
FIG. 13 is a flow chart showing the operation of the biosensor inspection device according to the third modification of the first embodiment.

However, such an inspection can also be performed by means of a third modification of the first embodiment described below with reference to FIGS. 12 and 13. The biosensor inspection device according to the third modification is obtained by replacing the reflectance changing unit 14 of the biosensor inspection device according to the first embodiment with a reflectance changing unit 14C shown in FIG. 12. FIG. 12 is a plan view showing the reflectance changing unit 14C of the biosensor inspection device according to the third modification. The reflectance changing unit 14C is a disk on which portions 14Ca, 14Cb each having a different reflectance are alternately printed in the circumferential direction. A portion 14Ca and a portion 14Cb having different reflectances make a pair, and a plurality of pairs each having a different cycle are printed on the reflectance changing unit 14C. For example, the reflectance changing unit 14C has a first cycle Dperiod1, a second cycle Dperiod2, a third cycle Dperiod3, and a fourth cycle Dperiod4 as shown in FIG. 12, and at least one of the cycles Dperiod1, Dperiod2, Dperiod3, Dperiod4 is different from the others. In FIG. 12, the disk has the relationship Dperiod1=Dperiod2<Dperiod3<Dperiod4. Although the disk shown in FIG. 12 has four cycles, the disk may have N, which is two or more, cycles. The reflectance change control unit 12 stores a table of the cycles Dperiod. In the following descriptions, the value the i-th period is denoted by Dperiod[i].

(Operation of Third Modification)

The operation of the biosensor inspection device according to the third modification will be described in detail with reference to a flow chart shown in FIG. 13.

The reflectance change control unit 12 set the position of the disk serving as the reflectance changing unit 14C at a zero point (step 201). A mechanism such as a limit switch may be used in the zero point setting.

Next, the reflectance change control unit 12 sends a command to the synchronization signal output unit 13 to output a synchronization signal. Receiving the command, the synchronization signal output unit 13 outputs a synchronization signal to the outside (step 202).

The reflectance change control unit 12 then transmits a drive signal to the reflectance changing unit 14C to drive the reflectance changing unit 14C. The reflectance change control unit 12 includes a first counter (not shown) for counting the number of times the drive signal is transmitted, and increments a first count value, Nd, of the first counter by 1 every time the drive signal is transmitted (step 203).

The reflectance change control unit 12 determines whether the first count value Nd reaches a first predetermined value (Nd_Limit) (step 204). Unlike the process shown in FIG. 7, the first predetermined value Nd_Limit is not a constant value but determined based on the number of cycles (see step 206 described later). The initial value of the first predetermined value Nd_Limit is, however, Dperiod[1]/Dd. If the first count value Nd reaches the first predetermined value Nd_Limit, the first count value Nd is reset, i.e. Nd=0 and the process proceeds to step 205. The reflectance change control unit 12 also includes a second counter (not shown) to store the number of times (second count value) Nbeat the cycle of the variation in reflectance changes, and increments the second count value Nbeat by 1 every time the first count value Nd of the first counter reaches the first predetermined value Nd_Limit. If the first count value Nd is not equal to the first predetermined value Nd_Limit, the process returns to step 203, and the aforementioned steps are repeated.

The reflectance change control unit 12 determines whether the second count value Nbeat reaches a second predetermined value (Nbeat_Limit) (step 205). The second predetermined value Nbeat_Limit is a predetermined constant. If the second count value Nbeat reaches the second predetermined value Nbeat_Limit, the process ends. If the second count value Nbeat is not equal to the second predetermined value Nbeat_Limit, the process proceeds to step 206.

Referring to the second count value Nbeat of the second counter storing the number of times the cycle of reflectance changes, the reflectance change control unit 12 updates the value of the first predetermined value Nd_Limit (step 206). The value of the first predetermined value Nd_Limit here is Nd_Limit=Dperiod[Nbeat]/Dd. Thereafter, the process returns to step 202, and the aforementioned steps are repeated.

Figure 14:
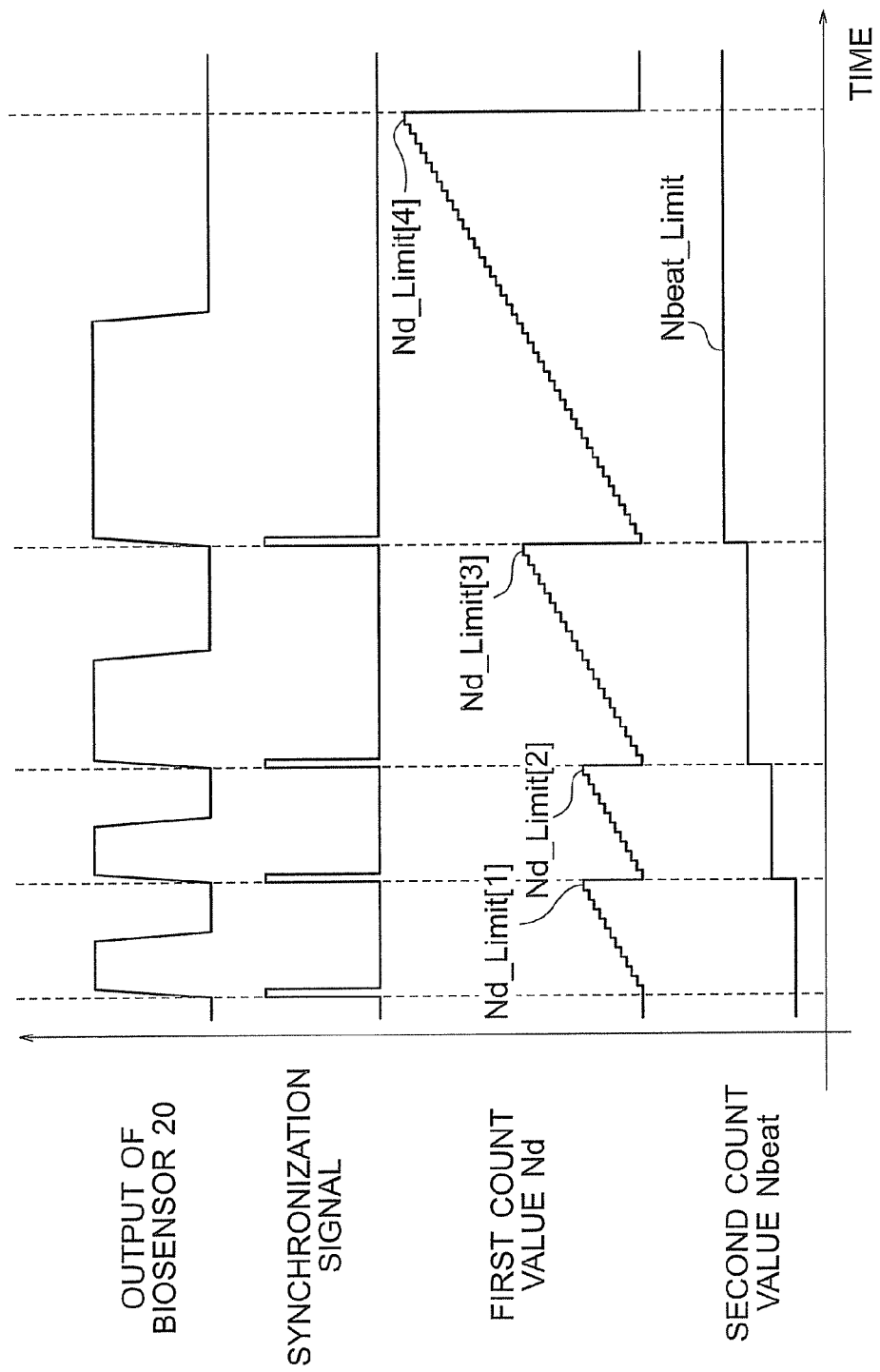
FIG. 14 shows waveforms of signals obtained by the third modification of the first embodiment.

As a result the above operation of the third modification, waveforms shown in FIG. 14 are obtained. The cycle of change in reflectance can be varied with the number of drive signals to be transmitted to the motor at step 203 being maintained constant. This means that the rotational speed of the motor for driving the reflectance changing unit 14C can be kept constant. Therefore, the frequency of vibrations caused to the biosensor inspection device according to the third modification does not change. As a result, it is possible to prevent changes in cycle of noise caused by vibrations when the numbers of pulses in different cycles are to be reproduced.

Figure 10:
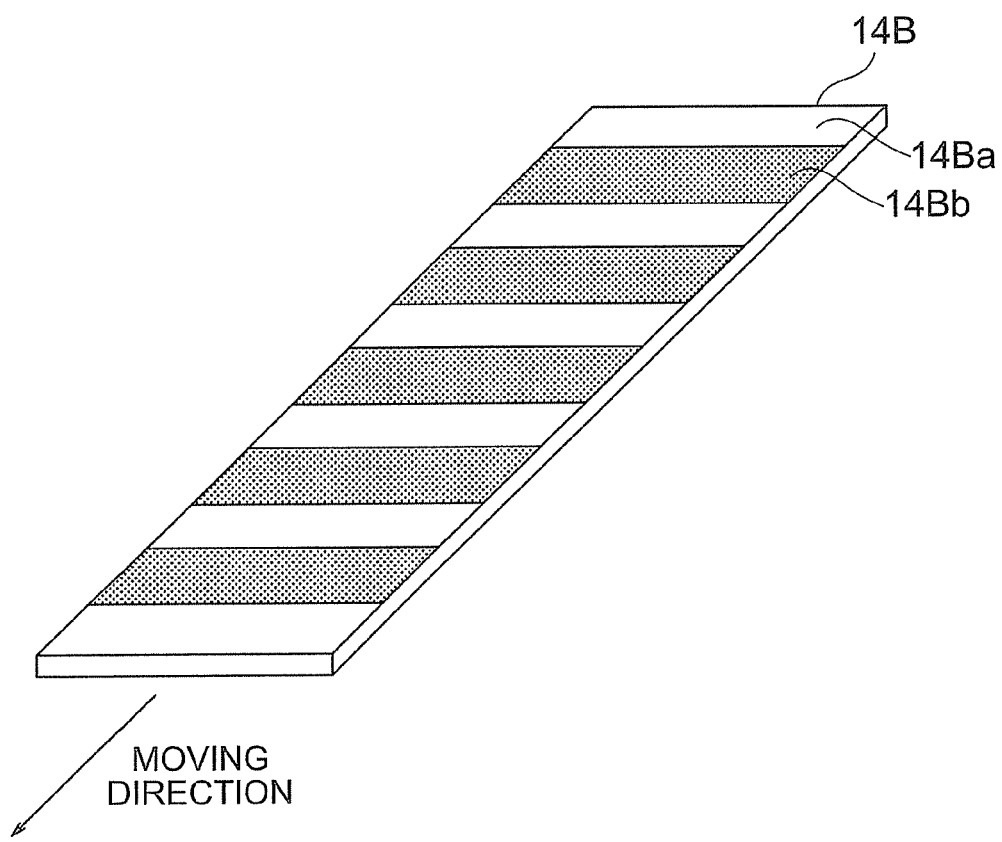
FIG. 10 is a perspective view of a reflectance changing unit of a second modification of the first embodiment.
Figure 11:
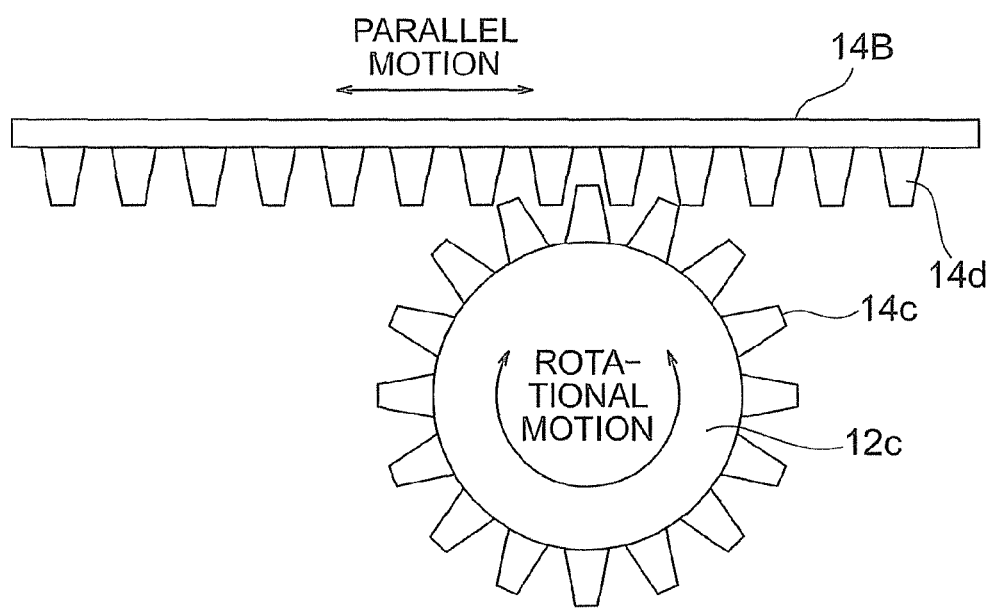
FIG. 11 is a diagram showing a mechanism of the reflectance changing unit of the second modification.

The third modification can be applied to the first modification shown in FIG. 9 and the second modification shown in FIG. 10.

(Fourth Modification)

Some biosensors have a function of measuring not only photoelectric pulse waves but also different biosignal waveforms such as those of electrocardiogram. Such biosensors are required to inspect whether photoelectric pulse waves and electrocardiogram waveforms are measured at the same time. A fourth modification described below may be used for such an application.

Figure 15:
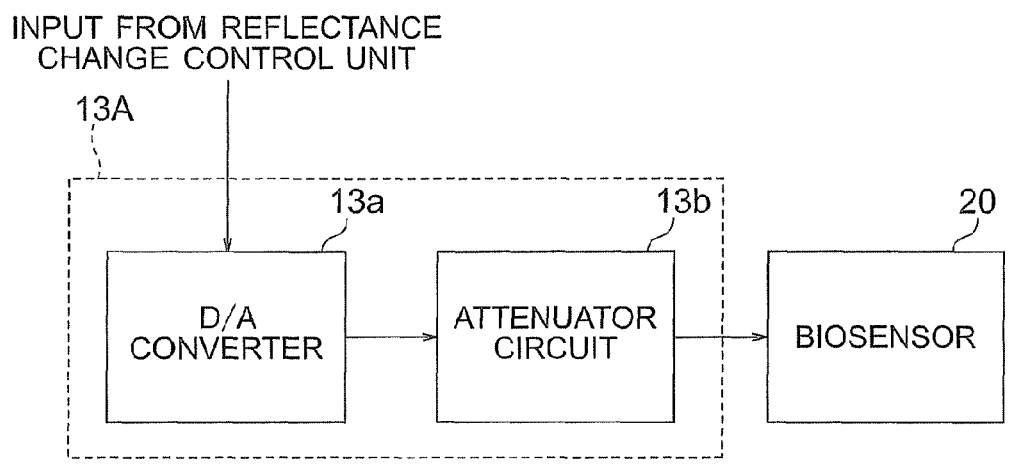
FIG. 15 is a block diagram showing a synchronization signal output unit of a fourth modification of the first embodiment.

The biosensor inspection device according to the fourth modification is obtained by replacing the synchronization signal output unit 13 of the biosensor inspection device according to the first embodiment with a synchronization signal output unit 13A shown in FIG. 15. FIG. 15 is a block diagram showing the synchronization signal output unit 13A of the fourth modification. The synchronization signal output unit 13A includes a digital-to-analog converter 13a and an attenuator circuit 13b. The digital-to-analog converter (D/A converter) 13a converts a digital signal from the reflectance change control unit 12 to an analog signal and outputs the analog signal. The amplitude of the analog signal is adjusted to be a few mV through the attenuator circuit 3b. Then, the analog signal is supplied to an electrocardiogram sensor of the biosensor 20.

The reflectance change control unit 12 of the fourth modification stores a table of electrocardiogram waveforms, and is capable of transmitting the contents of the table to the synchronization signal output unit 13A. The transmission protocol may be arbitrarily selected from a parallel transmission protocol on a TTL level, UART, I2C, SPI, and the like. The i-th value in the table will be described as ECG[i].

(Operation of Fourth Modification)

Figure 16:
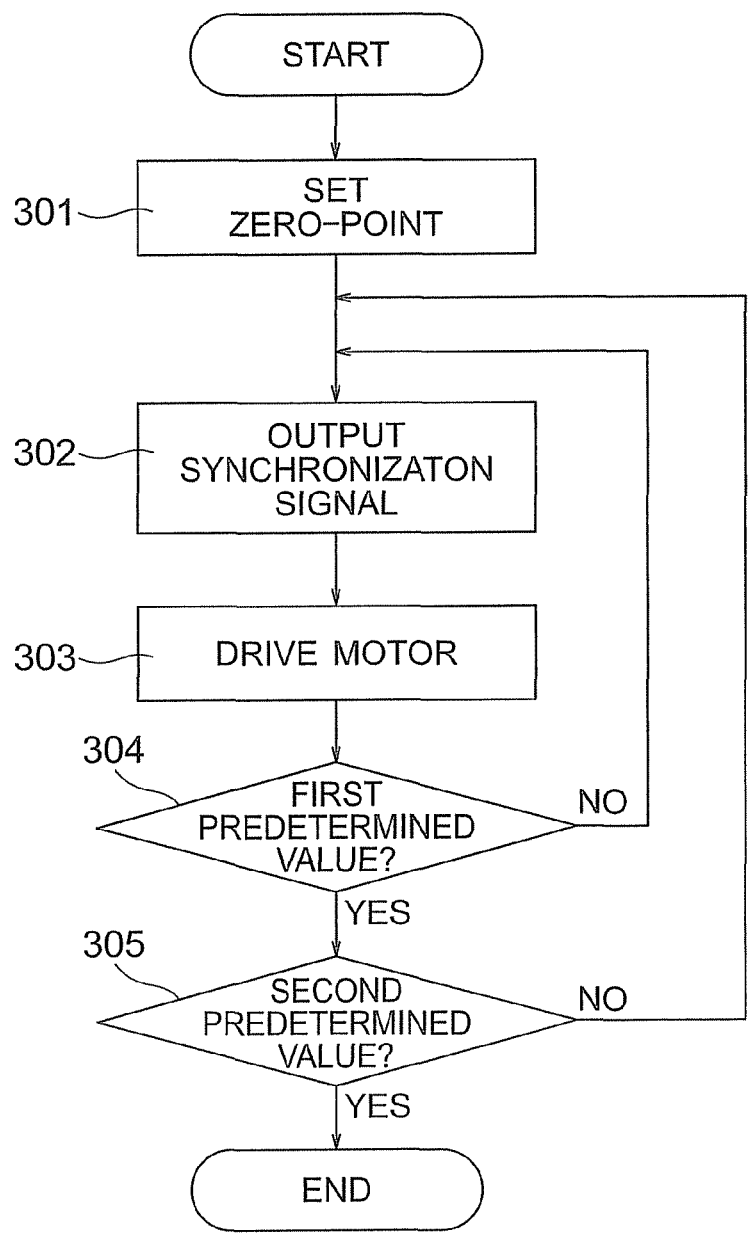
FIG. 16 is a flow chart for explaining the operation of the biosensor inspection device according to the fourth modification.

The operation of the fourth modification will be described with reference to a flow chart shown in FIG. 16.

First, the reflectance change control unit 12 sets the position of the reflectance changing unit 14 at a zero point (step 301). The zero-point setting may be performed by a certain mechanism such as a limit switch.

Next, the reflectance change control unit 12 transmits a command to the synchronization signal output unit 13A to output a synchronization signal. Receiving the command, the synchronization signal output unit 13A outputs a synchronization signal to the outside (step 302). The reflectance change control unit 12 then refers to a first count value Nd of a first counter for storing the number of times a drive signal is transmitted to the synchronization signal output unit 13A, and transmits a value of ECG[Nd] to the synchronization signal output unit 13A. The synchronization signal output unit 13A outputs the value of ECG[Nd] via the digital-to-analog converter 13a (step 302).

The reflectance change control unit 12 then transmits a drive signal to the reflectance changing unit 14 to drive the reflectance changing unit 14. The reflectance change control unit 12 increments the first count value Nd by 1 every time the drive signal is transmitted (step 303).

The reflectance change control unit 12 determines whether the first count value Nd reaches a first predetermined value (Nd_Limit) (step 304). Assuming that the disk serving as the reflectance changing unit 14 rotates by Dd degrees in response to a drive signal, and the magnitude of reflectance periodically changes in a cycle of Dperiod (degree) as shown in FIG. 4, the first predetermined value (Nd_Limit) is determined by Nd_Limit=Dperiod/Dd. If the first count value Nd reaches the first predetermined value Nd_Limit, the first count value Nd is reset, i.e., Nd=0, and the process proceeds to step 305. The reflectance change control unit 12 also includes a second counter (not shown) to store the number of times the cycle of variation in reflectance (second count value) Nbeat changes, and increments the second count value Nbeat by 1 every time the first count value Nd of the first counter reaches the first predetermined value Nd_Limit. If the first count value Nd is not equal to the first predetermined value Nd_Limit, the process returns to step 302, and the aforementioned steps are repeated.

The reflectance change control unit 12 determines whether the second count value Nbeat reaches a second predetermined value (Nbeat_Limit) (step 305). The second predetermined value Nbeat_Limit is a predetermined constant. If the second count value Nbeat reaches the second predetermined value Nbeat_Limit, the process ends. If the second count value Nbeat is not equal to the second predetermined value Nbeat_Limit, the process returns to step 302, and the aforementioned steps are repeated.

Figure 17:
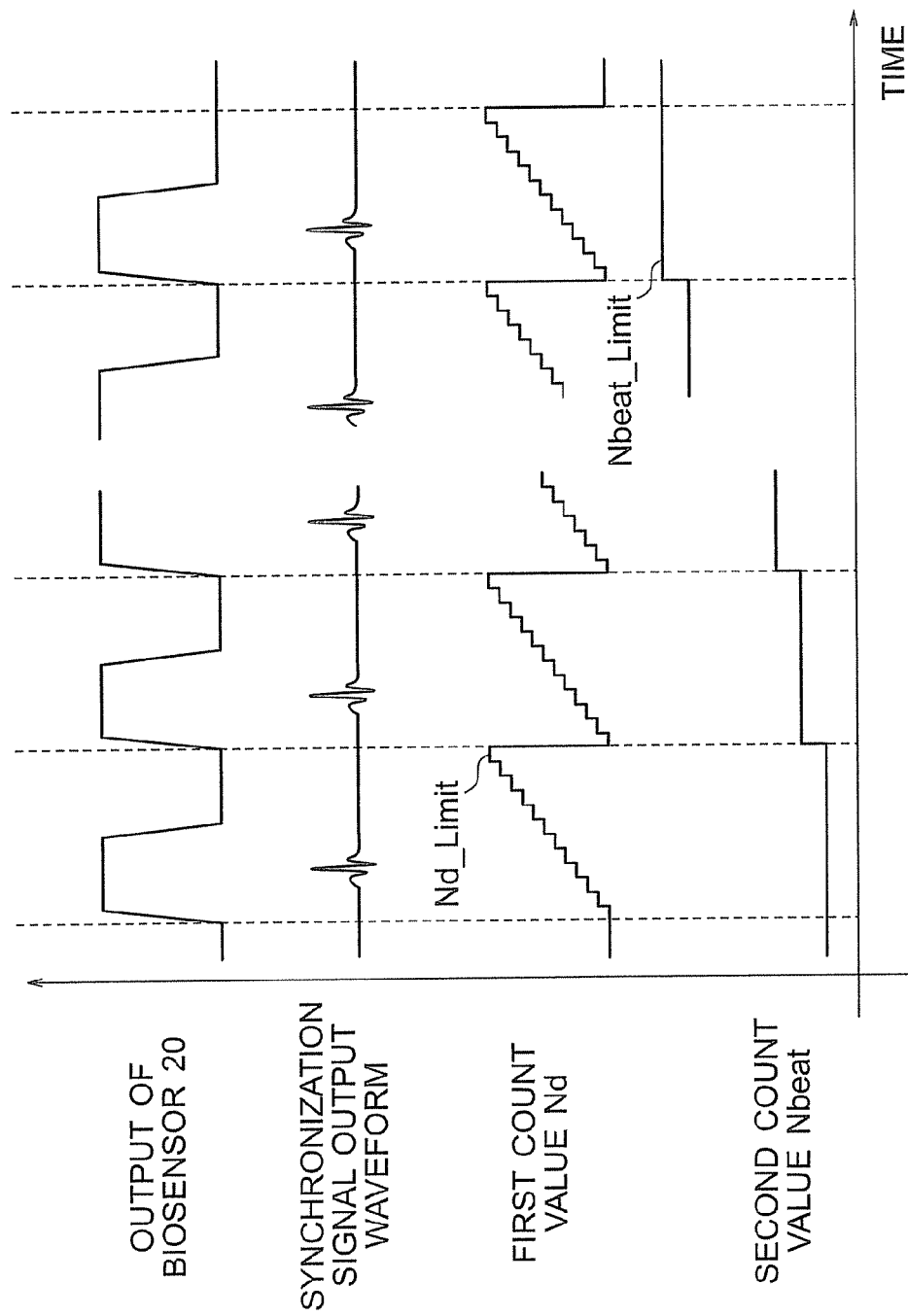
FIG. 17 shows waveforms of signals obtained by the fourth modification.

As a result, signal waveforms shown in FIG. 17 are obtained. An inspection as to whether the biosensor 20 has a desired performance with respect to electrocardiogram detection in addition to photoelectric pulse wave detection can be performed by checking the output of the biosensor 20.

Although an example of electrocardiogram is described as the fourth modification, inspections on the function of measuring other biosignals such as those in phonocardiogram (acoustic signals), impedance cardiography (electric resistance), and respiration (air flow) may be performed by outputting signals simulating such biosignals.

(Second Embodiment)

Figure 18:
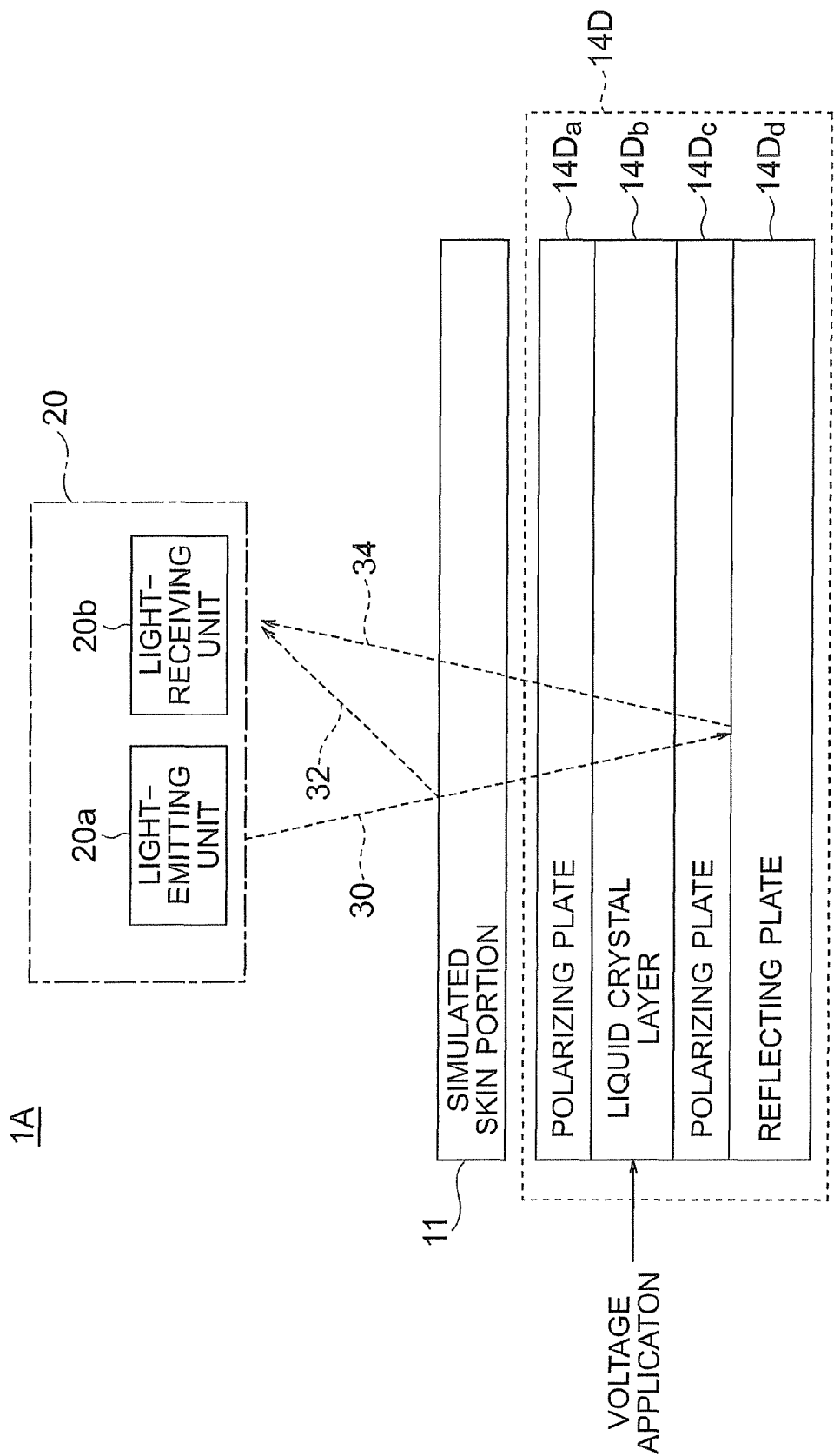
FIG. 18 is a block diagram showing a reflectance changing unit of a biosensor inspection device according to a second embodiment.

A biosensor inspection device according to a second embodiment will be described with reference to FIG. 18. FIG. 18 shows a reflectance changing unit 14D of the biosensor inspection device according to the second embodiment. The biosensor inspection device 1A according to the second embodiment inspects a photoelectric pulse wave sensor of reflection type 20 including a light-emitting unit 20a and a light-receiving unit 20b, and is obtained by replacing the reflectance changing unit 14 of the biosensor inspection device according to the first embodiment with the reflectance changing unit 14D. The reflectance of the material of the reflectance changing unit 14D changes in time series to simulate changes in amount of light incident to the light-receiving unit of the biosensor, the changes being in response to pulses of blood. In the second embodiment, the reflectance changing unit 14D is a liquid crystal display of reflection type, including a polarizing plate 14Da, a liquid crystal layer 14Db, a polarizing plate 14Dc, and a reflecting plate 14Dd.

Partial light 32 of light 30 emitted from the light-emitting unit 20a of the biosensor 20 is reflected on a simulated skin portion 11 and received by the light-receiving unit 20b of the biosensor 20. The rest of light 30 emitted from the light-emitting unit 20a passes through the simulated skin portion 11, the polarizing plate 14Da, the liquid crystal layer 14Db, and the polarizing plate 14Dc to reach and be reflected by the reflecting plate 14Dd. The reflected light 34 passes through the polarizing plate 14Dc, the liquid crystal layer 14Db, the polarizing plate 14Da, and the simulated skin portion 11 and is received by the light-receiving unit 20b. The amount of the reflected light 34 is varied in response to voltage applied to the liquid crystal layer 14Db. The voltage applied to the liquid crystal layer 14Db is determined by a signal transmitted from the reflectance change control unit 12.

The reflectance change control unit 12 controls the reflectance of the reflectance changing unit 14D to vary in time series. The reflectance change control unit 12 may include a microcomputer (not shown) and a liquid crystal driver circuit (not shown). The microcomputer is capable of controlling the reflectance of the reflectance changing unit 14D freely by transmitting signals to the liquid crystal driver circuit. The microcomputer includes a memory to store a table of predetermined liquid crystal control patterns.

The reflectance change control unit 12 also has a function of transmitting a signal in sync with the liquid crystal control to a synchronization signal output unit 13, which will be described later.

Figure 19:
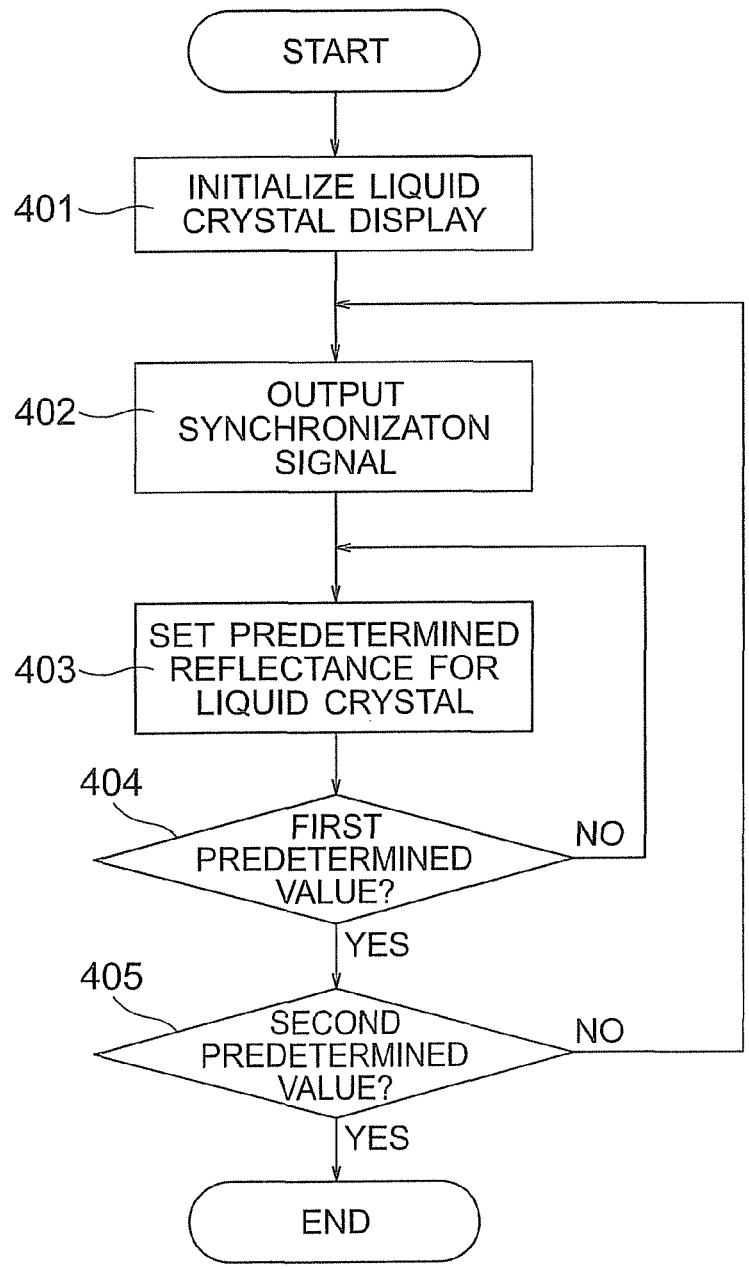
FIG. 19 is a flow chart for explaining the operation of the biosensor inspection device according to the second embodiment.

The operation of the biosensor inspection device 1A according to the second embodiment will be described with reference to a flow chart shown in FIG. 19.

First, the reflectance change control unit 12 set the reflectance of the liquid crystal layer 14Db of the reflectance changing unit 14D at a predetermined initial value (step 401).

Next, the reflectance change control unit 12 transmits a command to the synchronization signal output unit 13 to output a synchronization signal. Receiving the command, the synchronization signal output unit 13 outputs a synchronization signal to the outside (step 402).

The reflectance change control unit 12 then refers to a first count value Nr of a first counter (not shown) included therein, and applies a predetermined voltage to the liquid crystal layer 14Db of the reflectance changing unit 14D so that the reflectance has a value corresponding to the first count value Nr (step 403). The predetermined voltage has a value of one cycle of heart beat discretized by Nr_Limit, which is stored in the reflectance change control unit 12 in advance. The reflectance change control unit 12 also increments the first count value Nr stored therein by 1.

The reflectance change control unit 12 determines whether the count value Nr reaches a first predetermined value Nr_Limit (step 404). If the first count value Nr is equal to the first predetermined value Nr_Limit, the first count value Nr is reset to 0, and the process proceeds to step 405. The reflectance change control unit 12 also includes a second counter (not shown) of storing the number of times the cycle of variation in reflectance (Nbeat) changes, and increments the second count value Nbeat of the second counter by 1 every time the first count value Nr reaches the first predetermined value Nr_Limit. If the first count value Nr is not equal to the first predetermined value Nr_Limit, the process returns to step 403, and the aforementioned steps are repeated.

The reflectance change control unit 12 determines whether the second count value Nbeat reaches a second predetermined value (Nbeat_Limit) (step 405). The second predetermined value Nbeat_Limit is a predetermined constant. If the second count value Nbeat reaches the second predetermined value Nbeat_Limit, the process ends. If the second count value Nbeat is not equal to the second predetermined value Nbeat_Limit, the process returns to step 402, and the aforementioned steps are repeated.

As a result, signal waveforms similar to those shown in FIG. 8 are obtained. The first count value Nd and the first predetermined value Nd_Limit shown in FIG. 8, however, are replaced with the first count value Nr and the first predetermined value Nr_Limit, respectively. An inspection as to whether the biosensor 20 has a desired performance can be performed by checking the output of the biosensor 20.

Since no mechanical vibration that changes the reflectance is caused in the second embodiment, an inspection that is unlikely to be affected by noise caused by vibrations can be performed by controlling the reflectance in a cycle that is different from the cycle of natural frequency of the biosensor inspection device.

(Third Embodiment)

Figure 20:
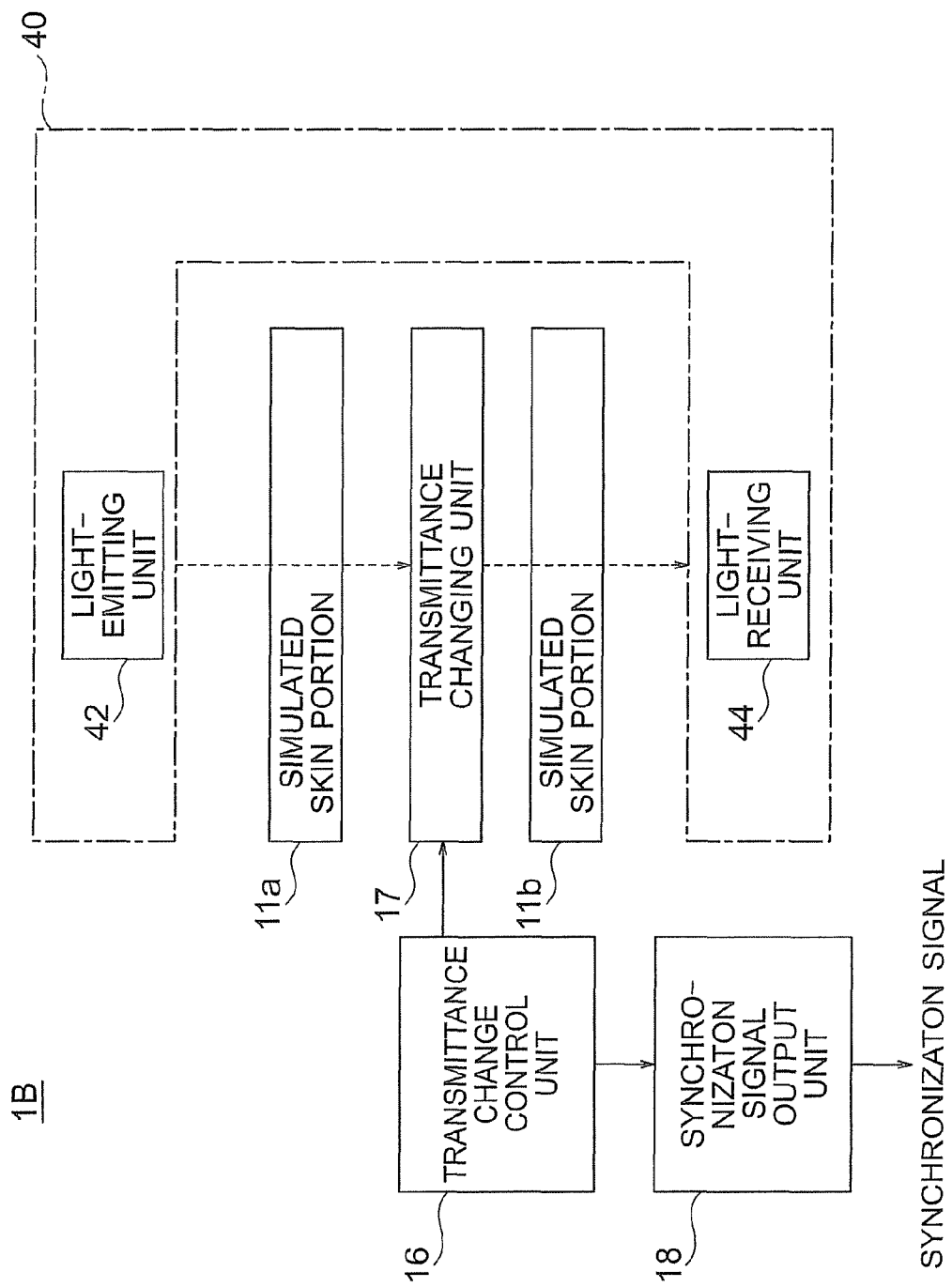
FIG. 20 is a block diagram showing a biosensor inspection device according to a third embodiment.

A biosensor inspection device according to a third embodiment will be described with reference to FIG. 20. FIG. 20 is a block diagram showing a biosensor inspection device according to the third embodiment. The biosensor inspection device 1B according to the third embodiment is for inspecting a photoelectric pulse wave sensor of transmission type (hereinafter also referred to a biosensor) 40 including a light-emitting unit 42 and a light-receiving unit 44. The biosensor inspection device includes simulated skin portions 11a, 11b, a transmittance change control unit 16, a transmittance changing unit 17, and a synchronization signal output unit 18.

The simulated skin portions 11a, 11b are located above and below the transmittance changing unit 17. They are formed of a material semitransparent to light, and preferably have a Lambertian characteristic. The simulated skin portions 11a, 11b may be replaceable depending on for whom the biosensor 40 is used. The simulated skin portions 11a, 11b simulate transmission and diffusion of light on a living body.

The transmittance changing unit 17 is formed of a material of which the transmittance varies in time series so as to simulate changes in amount of light incident on the light-receiving unit 44 of the biosensor 40 in response to pulses of blood. In the third embodiment, the transmittance changing unit 17 is a disk similar to that shown in FIG. 4, and portions with different transmittances are printed to be arranged along the circumferential direction of the disk. Thus, the transmittance changing unit 17 is obtained by replacing the portions 14a, 14b having different reflectances of the reflectance changing unit 14 shown in FIG. 4 with portions having different transmittances. Instead of printing, some elements formed of different materials may be bonded to the surface of the disk. The disk is driven by a stepping motor to rotate freely. Similarly, the transmittance changing unit may be formed by replacing the portions 14a, 14b having different reflectances in the reflectance changing unit of the second modification of the first embodiment shown in FIG. 10 or the reflectance changing unit of the third modification of the first embodiment shown in FIG. 12 with portions having different transmittances.

The transmittance change control unit 16 transmits a transmittance control signal to the transmittance changing unit 17 so as to change the transmittance of the transmittance changing unit 17 in time series. Like the reflectance change control unit of the first embodiment, the transmittance change control unit 16 may include a microcomputer, a motor driver circuit, and a stepping motor as shown in FIG. 3. The microcomputer is capable of controlling the rotations of the stepping motor freely by transmitting a drive signal to the motor driver circuit. Furthermore, the microcomputer includes a memory to store predetermined control patterns of the stepping motor. The transmittance change control unit 16 also has a function of transmitting to the synchronization signal output unit 18 a signal in sync with a transmittance control signal for controlling to the stepping motor.

The synchronization signal output unit 18 outputs a signal in sync with the change in the state of the transmittance changing unit 17, i.e., a signal in sync with changes in transmittance, to an external device in response to the transmittance control signal outputted from the transmittance change control unit 16. The synchronization signal outputted here may be a simple digital signal on a TTL level, or a signal in accordance with a generally known protocol such as UART, I2C, and SPI.

The light-emitting unit 42 and the light-receiving unit 44 of the biosensor 40 are arranged to have a substantially opposing positional relationship. The simulated skin portion 11a, the transmittance changing unit 17, and the simulated skin portion 11b are sandwiched by the light-emitting unit 42 and the light-receiving unit 44. Light emitted from the light-emitting unit 42 passes through the simulated skin portion 11a, the transmittance changing unit 17, and the simulated skin portion 11b, and reaches the light-receiving unit 42.

Figure 21:
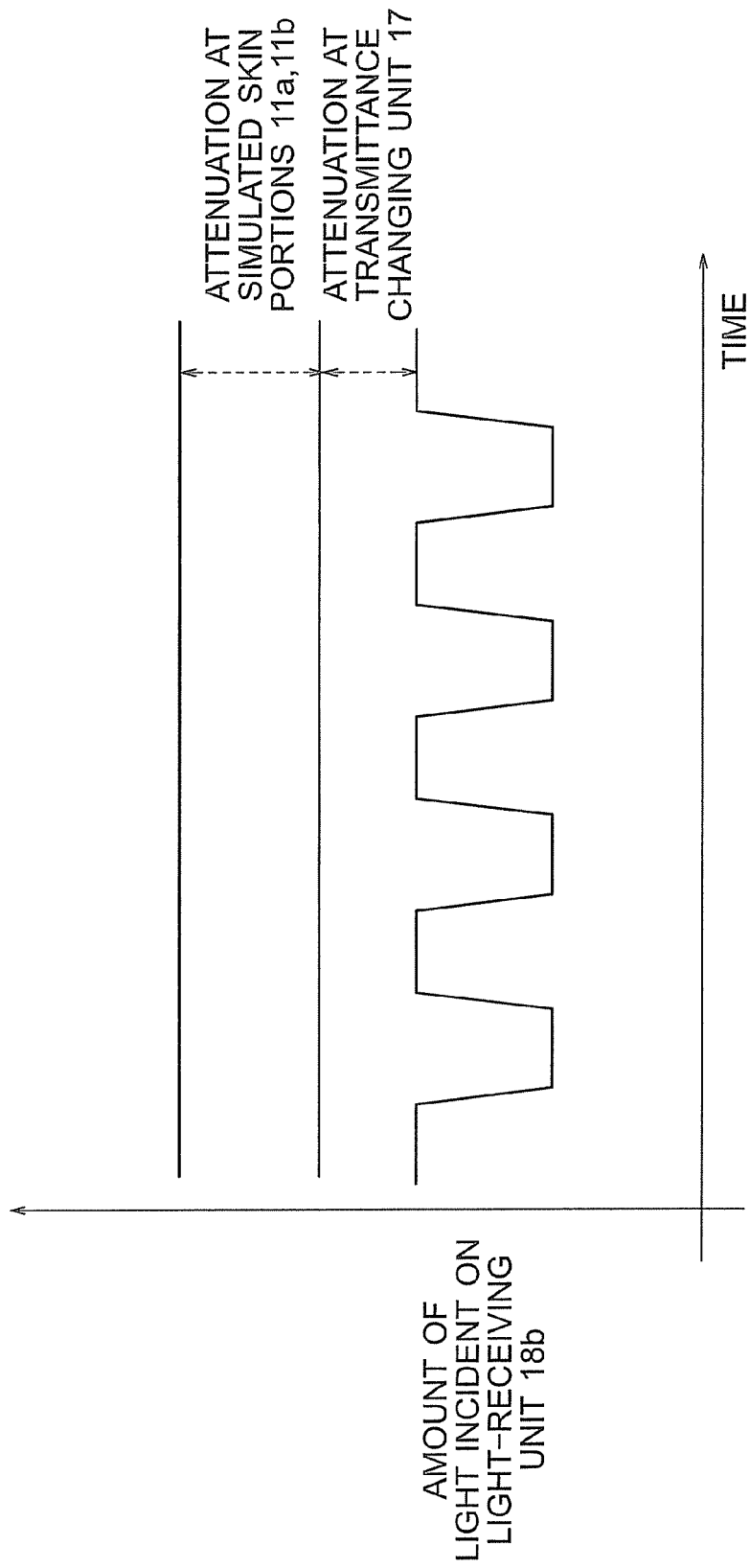
FIG. 21 shows waveforms of signals obtained by the biosensor inspection device according to the third embodiment.

If the reflectance changing unit 17 rotates, the light reaching the light-receiving unit 44 of the biosensor 40 changes in time series in response to the changes in transmittance of the transmittance changing unit 17 as shown in FIG. 21. This waveform becomes similar to that of a signal obtained from a photoelectric pulse wave sensor of transmission type 40 attached to an actual human body.

Figure 7:
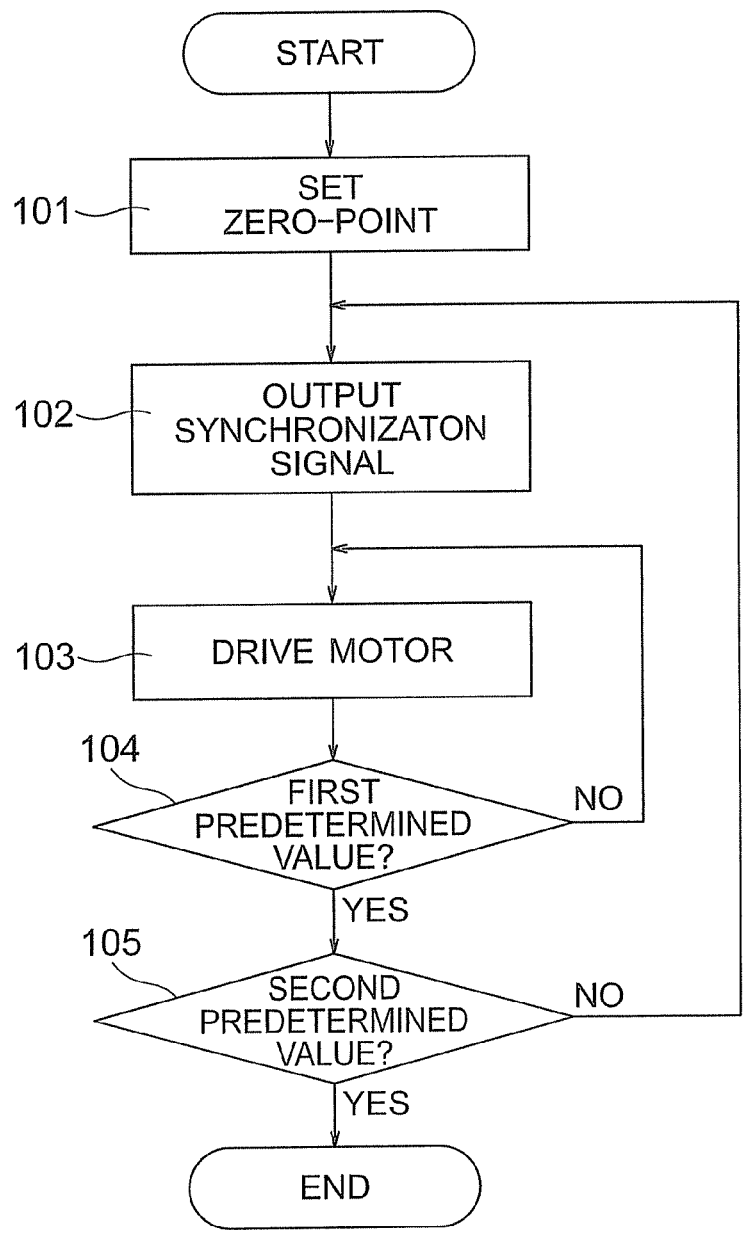
FIG. 7 is a flow chart for explaining the operation of the biosensor inspection device according to the first embodiment.

The operation of the biosensor inspection device according to the third embodiment is the same as that of the process flow of the first embodiment shown in FIG. 7 if the reflectance changing unit of the first embodiment is read as the transmittance changing unit.

As a result of such an operation, signal waveforms similar to those shown in FIG. 8 are obtained. An inspection as to whether the biosensor 40 of transmission type having a function of detecting photoelectric pulse waves has a desired performance can be performed by checking the output of the biosensor 40.

(Fourth Embodiment)

Figure 22:
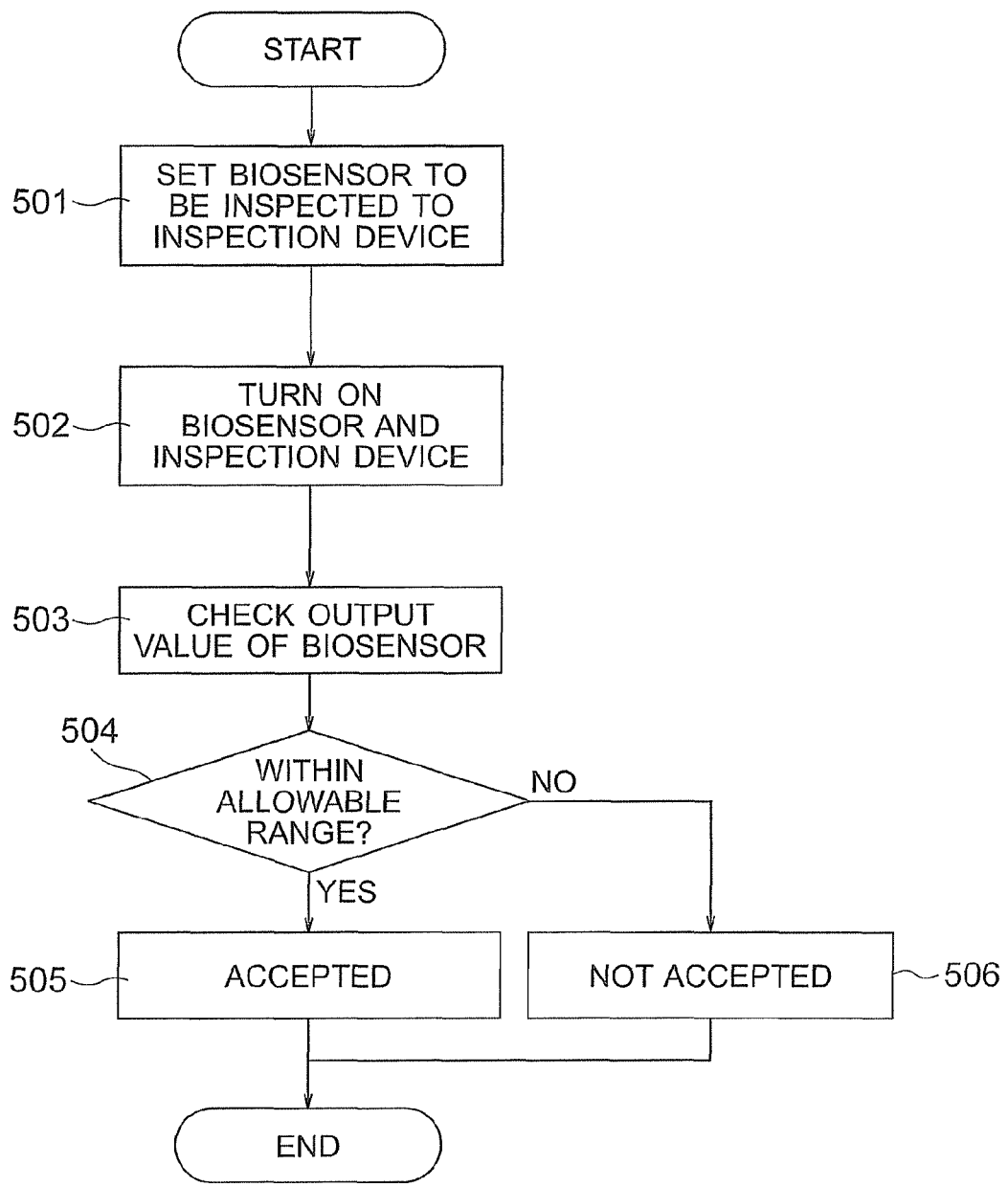
FIG. 22 is a flow chart showing a procedure of a biosensor inspection method according to a fourth embodiment.

A biosensor inspection method according to a fourth embodiment will be described with reference to FIG. 22. In the biosensor inspection method according to the fourth embodiment, a biosensor inspection device according to any of the first to third embodiments and their modifications is used to perform a biosensor inspection.

First, a biosensor to be inspected is placed on a biosensor inspection device (step 501). The biosensor inspection device is any of the biosensor inspection devices according to the first to third embodiments and their modifications. The biosensor is of at least reflection or transmission type having a function of detecting the number of pulses.

Next, the biosensor to be inspected is turned on, so that the output value of the biosensor can be checked. The biosensor inspection device is also turned on (step 502). Then, the biosensor inspection device performs the process according to any of the first to the third embodiments or their modifications to input simulated biosignals to the biosensor.

Thereafter, the output value of the biosensor is checked (step 503). Means for checking the output value may be a common waveform monitor such as an oscilloscope or, if the output value is that of a serial communication signal, a device having a function of receiving signals according to a corresponding protocol. The synchronization signal outputted from the biosensor inspection device is also checked.

Next, whether the values of amplitude and frequency of a signal outputted from the biosensor, the value of phase difference between the synchronization signal outputted from the biosensor inspection device and the output signal of the biosensor, and the value calculated based on these values are within allowable ranges is checked (step 504). The allowable ranges are predetermined. If the output value of the biosensor is within the allowable range, the process proceeds to step 505 and if it is outside the allowable value, the process proceeds to step 506.

At step 505, the biosensor is determined to meet predetermined performance standard, and pass the inspection.

At step 506, the biosensor is determined not to meet predetermined performance standard, and fail the inspection.

The described process may be automatically and mechanically performed. Through the aforementioned procedure, whether the biosensor has predetermined performance can be inspected.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

A method for inspecting a photoelectric pulse wave sensor of reflection type comprising: emitting light to be incident on a simulated skin portion semitransparent to light, the simulated skin portion being arranged near the photoelectric pulse wave sensor and simulating a blood flow of the skin; measuring reflected light from the simulated skin portion, and also measuring reflected light that passes through the simulated skin portion and is reflected from a reflectance changing unit located on an opposite side of the simulated skin portion to the photoelectric pulse wave sensor, the reflectance changing unit being capable of changing, in time series, reflectance of the light passing through the simulated skin portion; and determining whether the photoelectric pulse wave sensor is in normal operation based on the reflected light measured.

A method for inspecting a photoelectric pulse wave sensor of transmission type comprising: emitting light from the photoelectric pulse wave sensor toward an inspection device including a first simulated skin portion semitransparent to light, which receives the light from the photoelectric pulse wave sensor and simulates a blood flow of the skin, a transmittance changing unit that changes transmittance of the light passing through the first simulated skin portion in time series, and a second simulated skin portion that receives the light passing through the transmittance changing unit and simulates the blood flow of the skin; measuring the light passing through the first simulated skin portion, the transmittance changing unit, and the second simulated skin portion; and determining whether the photoelectric pulse wave sensor is in normal operation based on the transmitted light measured.

The invention claimed is:

1. A device for inspecting a photoelectric pulse wave sensor of reflection type comprising:
   a simulated skin portion semitransparent to light, the simulated skin portion being located near the photoelectric pulse wave sensor to simulate a blood flow of the skin;
   a reflectance changing unit located on an opposite side of the simulated skin portion to the photoelectric pulse wave sensor, the reflectance changing unit changing, in time series, reflectance of light emitted from a light-emitting unit of the photoelectric pulse wave sensor and passing through the simulated skin portion;
   a reflectance change control unit that transmits a reflectance control signal to the reflectance changing unit to control changes in reflectance of the reflectance changing unit; and
   a synchronization signal output unit that outputs a signal in sync with the reflectance control signal to an external device.

2. The device according to claim 1, wherein the reflectance changing unit is a rotating member including at least two portions each having a different reflectance, the at least two portions being arranged in a rotating direction, and wherein there are at least two cycles of changes in reflectance of the at least two portions in the rotating member.

3. The device according to claim 1, wherein the reflectance changing unit is a movable member including at least two portions each having a different reflectance, the at least two portions being arranged in a moving direction, and wherein there are at least two cycles of changes in reflectance of the at least two portions in the movable member.

4. The device according to claim 2, wherein at least one of the at least two cycles is different from the other cycles.

5. The device according to claim 1, wherein the reflectance changing unit is a liquid crystal display of reflection type.

6. The device according to claim 1, wherein the synchronization signal output unit outputs a signal waveform simulating a biosignal other than that of photoelectric pulse waves.

7. A device for inspecting a photoelectric pulse wave sensor of transmission type comprising:
   a first simulated skin portion semitransparent to light, the first simulated skin portion being arranged between a light-emitting unit and a light-receiving unit of the photoelectric pulse wave sensor to simulate a blood flow of the skin, and a second simulated skin portion semitransparent to light, the second simulated skin portion being arranged between the first simulated skin portion and the light-receiving unit to simulate the blood flow of the skin;
   a transmittance changing unit arranged between the first simulated skin portion and the second simulated skin portion to change, in time series, transmittance of light emitted from the light-emitting unit of the photoelectric pulse wave sensor and passing through the first simulated skin portion;
   a transmittance change control unit that transmits a transmittance control signal to the transmittance changing unit to control changes in transmittance of the transmittance changing unit; and
   a synchronization signal output unit that outputs a signal in sync with the transmittance control signal to an external device.

8. The device according to claim 7, wherein the transmittance changing unit is a rotating member including at least two portions each having a different transmittance, the at least two portions being arranged in a rotating direction, and wherein there are at least two cycles of changes in transmittance of the at least two portions in the rotating member.

9. The device according to claim 8, wherein at least one of the at least two cycles is different from the other cycles.

10. The device according to claim 7, wherein the transmittance changing unit is a movable member including at least two portions each having a different transmittance, the at least two portions being arranged in a moving direction, and wherein there are at least two cycles of changes in transmittance of the at least two portions in the movable member.

11. The device according to claim 7, wherein the synchronization signal output unit outputs a signal waveform simulating a biosignal other than that of photoelectric pulse waves.

* * * * *